US008415527B2

(12) United States Patent
Gilbertson et al.

(10) Patent No.: US 8,415,527 B2
(45) Date of Patent: Apr. 9, 2013

(54) DNA CONSTRUCTS AND METHODS TO ENHANCE THE PRODUCTION OF COMMERCIALLY VIABLE TRANSGENIC PLANTS

(75) Inventors: Larry A. Gilbertson, Chesterfield, MO (US); Elysia K. Krieger, Kirkwood, MO (US); Wanggen Zhang, Wildwood, MO (US); Xudong Ye, Madison, WI (US)

(73) Assignee: Monsanto Technology LLC, St. Louis, MO (US)

( * ) Notice: Subject to any disclaimer, the term of this patent is extended or adjusted under 35 U.S.C. 154(b) by 552 days.

(21) Appl. No.: 12/542,586

(22) Filed: Aug. 17, 2009

(65) Prior Publication Data

US 2009/0328253 A1    Dec. 31, 2009

Related U.S. Application Data

(62) Division of application No. 10/821,711, filed on Apr. 8, 2004, now Pat. No. 7,575, 917.

(60) Provisional application No. 60/461,459, filed on Apr. 9, 2003.

(51) Int. Cl.
*C12N 15/84* (2006.01)
*C12N 15/53* (2006.01)
*A01H 1/04* (2006.01)

(52) U.S. Cl. ........ 800/294; 800/290; 800/300; 435/189; 435/320.1; 435/430.1; 435/469

(58) Field of Classification Search ........................ None
See application file for complete search history.

(56) References Cited

U.S. PATENT DOCUMENTS

| 5,702,933 | A | * | 12/1997 | Klee et al. | ...................... | 800/283 |
| 5,939,539 | A | | 8/1999 | Lange et al. | ...................... | 536/23.2 |
| 6,521,458 | B1 | | 2/2003 | Gutterson et al. | ............ | 435/469 |
| 6,767,735 | B1 | * | 7/2004 | Sugita et al. | ............... | 435/320.1 |
| 7,303,909 | B2 | | 12/2007 | Heim et al. | ..................... | 800/294 |
| 7,749,751 | B2 | | 7/2010 | Depicker et al. | ............. | 435/325 |
| 2002/0133850 | A1 | * | 9/2002 | Clendennen et al. | ........ | 800/287 |
| 2003/0140376 | A1 | | 7/2003 | Depicker et al. | ............. | 435/325 |

FOREIGN PATENT DOCUMENTS

| CA | 2477240 | 8/2003 |
| CA | 2479739 | 10/2003 |
| EP | 0 716 147 | 6/1996 |
| EP | 1 033 409 | 9/2000 |
| EP | 1 009 842 | 5/2004 |
| EP | 1 140 043 | 3/2005 |
| JP | 9-154580 | 6/1997 |
| JP | 2001-218583 | 8/2001 |
| JP | 2002-514927 | 5/2002 |
| WO | WO 97/14807 | 4/1997 |
| WO | WO 99/01563 | 1/1999 |
| WO | WO 01/44482 | 6/2001 |
| WO | WO 01/96580 | * 12/2001 |
| WO | WO 03/069980 | 8/2003 |
| WO | WO 03/079765 | 10/2003 |

OTHER PUBLICATIONS

Coles et al., "Modification of gibberellin production and plant development in arabidopsis by sense and antisense expression of gibberellin 20-oxidase genes," *Plant J.*, 17(5):547-558, 1999.
Fray et al., "Constitutive expression of a fruit phytoene synthase gene in transgenic tomatoes causes dwarfism by redirecting metabolites from the gibberellin pathway," *Plant J.*, 8(5):693-701, 1995.
Lange et al., "Cloning and expression of a gibberellin 2β,3β-hydroxylase cDNA from pumpkin endosperm," *Plant Cell*, 9:1459-1467, 1997.
Romero et al., "Expression of the yeast trehalos-6-phosphate synthase gene in transgenic tobacco plants: pleiotropic phenotypes include drought tolerance," *Planta*, 201:293-297, 1997.
Sonnewald et al., "Transgenic tobacco plants expressing yeast-derived invertase in either the cytosol, vacuole or apoplast: a powerful tool for studying sucrose metabolism and sink/source interactions." *The Plant J.*, 1(1):95-106, 1991.
Ye et al., "Altered fructan accumulation in transgenic lolium multiflorum plants expressing a *Bacillus subtilis* sacB gene," *Plant Cell Rep.*, 20:205-212, 2001.
Ebinuma et al., "Selection of marker-free transgenic plants using the isopentenyl transferase gene," *Proc. Natl. Acad. Sci. USA*, 94:2117-2121, 1997.
Endo et al., "Single-step transformation for generating marker-free transgenic rice using the ipt-type MAT vector system," *The Plant J.*, 30:115-122, 2002.
Hanson et al., "A simple method to enrich an agrobacterium-transformed population for plants containing only T-DNA sequences," *The Plant J.*, 19:727-734, 1999.
Hedden et al., "Gibberellin metabolism: new insights revealed by the genes," *Trends in Plant Science*, 5(12):523-530, 2000.
Hedden, "Recent advances in gibberellin biosynthesis," *J. of Experimental Botany*, 50(334):553-563, 1989.
Sugita et al., "A transformation vector for the production of marker-free transgenic plants containing a single copy transgene at high frequency," *The Plant J.*, 22:461-469, 2000.
Ye et al., "Plant development inhibitory genes in binary vector backbone improve quality event efficiency in soybean transformation," *Transgenic Res.*, 17:827-838, 2008.

* cited by examiner

*Primary Examiner* — David T Fox
(74) *Attorney, Agent, or Firm* — SNR Denton US LLP; Thomas P. McBride, Esq.

(57) ABSTRACT

The present invention has incorporated a non-lethal negative selectable marker gene into the vector backbone DNA of a DNA plasmid used to transform plant cells. These transgenes are designed to express a non-lethal gene product in plant cells that contain the vector backbone DNA of the DNA plasmid. The gene products of the non-lethal negative selectable marker gene are involved in plant hormone biosynthesis pathways, plant hormone substrate diversion, plant hormone degradation, plant hormone signaling or metabolic interference. The use of these DNA plasmids to transform plant cells provides for the enhanced production of commercially viable plants.

8 Claims, 26 Drawing Sheets

SEQUENCE LISTING

<160> NUMBER OF SEQ ID NOS: 16

<210> SEQ ID NO 1
<211> LENGTH: 930
<212> TYPE: DNA
<213> ORGANISM: Erwinia herbicola

<400> SEQUENCE: 1

```
atgagccaac cgccgctgct tgaccacgcc acgcagacca tggccaacgg ctcgaaaagt      60
tttgccaccg ctgcgaagct gttcgacccg gccacccgcc gtagcgtgct gatgctctac     120
acctggtgcc gccactgcga tgacgtcatt gacgaccaga cccacggctt cgccagcgag     180
gccgcggcgg aggaggaggc cacccagcgc ctggcccggc tgcgcacgct gaccctggcg     240
gcgtttgaag gggccgagat gcaggacccg gccttcgctg cctttcagga ggtggcgctg     300
acccacggta ttacgccccg catggcgctc gatcacctcg acggctttgc gatggacgtg     360
gctcagaccc gctatgtcac cttttgaggat acgctgcgct actgctatca cgtggcgggc     420
gtggtgggtc tgatgatggc cagggtgatg ggcgtgcggg atgagcgggt gctggatcgc     480
gcctgcgatc tggggctggc cttccagctg acgaatatcg cccgggatat tattgacgat     540
gcggctattg accgctgcta tctgcccgcc gagtggctgc aggatgccgg gctgaccccg     600
gagaactatg ccgcgcggga gaatcgggcc gcgctggcgc gggtggcgga gcggcttatt     660
gatgccgcag agccgtacta catctcctcc caggccgggc tacacgatct gccgccgcgc     720
tgcgcctggg cgatcgccac cgcccgcagc gtctaccggg agatcggtat taaggtaaaa     780
gcggcgggag gcagccgcctg ggatcgccgc cagcacacca gcaaaggtga aaaaattgcc     840
atgctgatgg cggcaccggg gcaggttatt cgggcgaaga cgacgagggt gacgccgcgt     900
ccggccggtc tttggcagcg tcccgtttag                                       930
```

<210> SEQ ID NO 2
<211> LENGTH: 723
<212> TYPE: DNA
<213> ORGANISM: Agrobacterium tumefaciens

<400> SEQUENCE: 2

```
atggatctgc gtctaatttt cggtccaact tgcacaggaa agacgtcgac cgcggtagct      60
cttgcccagc agactgggct tccagtcctt tcgctcgatc gggtccaatg ttgtcctcag     120
ctgtcaaccg gaagcggacg accaacagtg gaagaactga aggaacgag ccgtctatac      180
cttgatgatc ggcctctggt gaagggtatc atcgcagcca agcaagctca tgaaaggctg     240
atggggagg tgtataatta tgaggcccac ggcgggctta ttcttgaggg aggatctatc     300
tcgttgctca agtgcatggc gcaaagcagt tattggagtg cggattttcg ttggcatatt     360
attcgccacg agttagcaga cgaagagacc ttcatgaacg tggccaaggc cagagttaag     420
cagatgttac gccctgctgc aggccttttct attatccaag agttggttga tctttggaaa     480
gagcctcggc tgaggcccat actgaaagag atcgatggat atcgatatgc catgttgttt     540
gctagccaga accagatcac atccgatatg ctattgcagc ttgacgcaga tatggaggat     600
aagttgattc atgggatcgc tcaggagtat ctcatccatg cacgccgaca agaacagaaa     660
ttccctcgag ttaacgcagc cgcttacgac ggattcgaag gtcatccatt cggaatgtat     720
tag                                                                    723
```

<210> SEQ ID NO 3

```
<211> LENGTH: 999
<212> TYPE: DNA
<213> ORGANISM: Phaseolus coccineus

<400> SEQUENCE: 3
atggttgttc tgtctcagcc agcattgaac cagttttttcc ttctgaaacc attcaagtcc      60
acgcccttgt tcacggggat tcctgtggtc gacctcacgc accccgatgc caagaatctc     120
atagtgaacg cctgtaggga cttcggcttc ttcaagcttg tgaaccatgg tgttccattg     180
gagttaatgg ccaatttaga aaacgaggcc ctcaggttct ttaaaaaatc tcagtccgag     240
aaagacagag ctggtccccc cgaccctttc ggctatggta gcaagaggat tggcccaaac     300
ggtgatgtcg gttgggtcga atacctcctc ctcaacacca accctgatgt tatctcaccc     360
aaatcacttt gcattttccg agaaaatcct catcatttca gggcggtggt ggagaactac     420
attacagcag tgaagaacat gtgctatgcg gtgttggaat tgatggcgga ggggttgggg     480
ataaggcaga ggaatacgtt aagcaggttg ctgaaggatg agaaaagtga ttcgtgcttc     540
aggttgaacc actacccgcc ttgccctgag gtgcaagcac tgaaccggaa ttttggttggg    600
tttggggagc acacagaccc acagataatt tctgtcttaa gatctaacag cacatctggc     660
ttgcaaatct gtctcacaga tggcacttgg gtttcagtcc cacctgatca gacttccttt     720
ttcatcaatg ttggtgacgc tctacaggta atgactaatg ggaggtttaa aagtgtaaag     780
catagggttt tggctgacac aacgaagtca aggttatcaa tgatctactt tggaggacca     840
gcgttgagtg aaaatatagc acctttacct tcagtgatgt taaaaggaga ggagtgtttg     900
tacaaagagt tcacatggtg tgaatacaag aaggctgcgt acacttcaag gctagctgat     960
aataggcttg ccccttttcca gaaatctgct gctgattaa                           999

<210> SEQ ID NO 4
<211> LENGTH: 1605
<212> TYPE: DNA
<213> ORGANISM: Zea mays

<400> SEQUENCE: 4
atggcggtgg tttattacct gctgctggcc gggctgatcg cctgctctca tgcactagcg      60
gcaggcacgc ctgcgctcgg agacgatcgc ggccgtccct ggccagcctc cctcgccgcg     120
ctggccttgg acggcaagct ccggaccgac agcaacgcga cggcggcggc ctcgacggac     180
ttcggcaaca tcacgtcggc gctcccggcg gcggtcctgt accgtcgtc cacgggcgac      240
ctggtggcgc tgctgagcgc ggccaactcc accccgggt ggccctacac catcgcgttc       300
cgcggccgcg gccactccct catgggccag gccttcgccc ccggcggcgt cgtcgtcaac     360
atggcgtccc tggcgacgc cgccgcgccg cgcgcatca acgtgtccgc ggacggccgc        420
tacgtggacg ccggcggcga gcaggtgtgg atcgacgtgt gcgcgcgtc gctggcgcgc       480
ggcgtggcgc gcgcgctcctg gaccgactac ctctacctca ccgtcggcgg cacgctgtcc     540
aacgcaggca tcagcggcca ggcgttccgc cacggcccac agatatctaa cgtgctggag     600
atggacgtta tcaccggtca tgggggagatg gtgacgtgct ccaagcagct gaacgcggac    660
ctgttcgacg ccgtcctggg cgggctgggg cagttcggag tgatcacccg gccccggatc     720
gcggtggagc cggcgccggc gcgggcgcgg tgggtgcggc tcgtgtacac cgacttcgcg     780
gcgttcagcg ccgaccagga gcggctgacc gccccgcggc ccggcggcgg cggcgcgtcg     840
ttcggcccga tgagctacgt ggaagggtcg gtgttcgtga accagagcct ggcgaccgac     900
ctggcgaaca cggggttctt caccgacgcc gacgtcgccc ggatcgtcgc gctcgccggg     960
```

```
gagcggaacg ccaccaccgt gtacagcatc gaggccacgc tcaactacga caacgccacg    1020
gcggcggcgg cggcggtgga ccaggagctc gcgtccgtgc tgggcacgct gagctacgtg    1080
gaggggttcg cgttccagcg cgacgtggcc tacgcggcgt tccttgaccg ggtgcacggc    1140
gaggaggtgg cgctcaacaa gctggggctg tggcgggtgc cgcacccgtg gctcaacatg    1200
ttcgtgccgc gctcgcgcat cgccgacttc gaccgcggcg tgttcaaggg catcctgcag    1260
ggcaccgaca tcgtcggccc gctcatcgtc taccccctca acaaatccat gtgggacgac    1320
ggcatgtcgg cggcgacgcc gtctgaggac gtgttctacg cggtgtcgct gctcttctcg    1380
tcggtggcgc ccaacgacct ggcgaggctg caggagcaga acaggaggat cctgcgcttc    1440
tgcgacctcg ccgggatcca gtacaagacc tacctggcgc ggcacacgga ccgcagtgac    1500
tgggtccgcc acttcggcgc cgccaagtgg aatcgcttcg tggagatgaa gaacaagtac    1560
gaccccaaga ggctgctctc ccccggccag gacatcttca actga                    1605

<210> SEQ ID NO 5
<211> LENGTH: 1605
<212> TYPE: DNA
<213> ORGANISM: Bacillus subtilis

<400> SEQUENCE: 5
atggcggtgg tttattacct gctgctggcc gggctgatcg cctgctctca tgcactagcg      60
gcaggcacgc ctgcgctcgg agacgatcgc ggccgtccct ggccagcctc cctcgccgcg     120
ctggccttgg acggcaagct ccggaccgac agcaacgcga cggcggcggc ctcgacggac     180
ttcggcaaca tcacgtcggc gctcccggcg gcggtcctgt accgtcgtc cacgggcgac      240 ctggtggcgc tgctgagcgc ggccaactcc accccggggt ggccctacac catcgcgttc     300
cgcggccgcg gccactccct catgggccag gccttcgccc ccgcggcgt cgtcgtcaac      360 atggcgtccc tgggcgacgc cgccgcgccg ccgcgcatca acgtgtccgc ggacggccgc     420
tacgtggacg ccgcggcgga gcaggtgtgg atcgacgtgt gcgcgcgtc gctggcgcgc      480 ggcgtggcgc cgcgctcctg gaccgactac ctctacctca ccgtcggcgg cacgctgtcc     540
aacgcaggca tcagcggcca ggcgttccgc cacggcccac agatatctaa cgtgctggag     600
atggacgtta tcaccggtca tggggagatg gtgacgtgct ccaagcagct gaacgcggac     660
ctgttcgacg ccgtcctggg cgggctgggg cagttcggag tgatcacccg ggcccggatc     720
gcggtggagc cggcgccggc cgggcgcgg tgggtgcggc tcgtgtacac cgacttcgcg      780
gcgttcagcg ccgaccagga gcggctgacc gccccgcgcc ccggcggcgg cggcgcgtcg     840
ttcggcccga tgagctacgt ggaagggtcg gtgttcgtga ccagagcct ggcgaccgac      900 ctggcgaaca cggggttctt caccgacgcc gacgtcgccc ggatcgtcgc gctcgccggg     960
gagcggaacg ccaccaccgt gtacagcatc gaggccacgc tcaactacga caacgccacg    1020
gcggcggcgg cggcggtgga ccaggagctc gcgtccgtgc tgggcacgct gagctacgtg    1080
gaggggttcg cgttccagcg cgacgtggcc tacgcggcgt tccttgaccg ggtgcacggc    1140
gaggaggtgg cgctcaacaa gctggggctg tggcgggtgc cgcacccgtg gctcaacatg    1200
ttcgtgccgc gctcgcgcat cgccgacttc gaccgcggcg tgttcaaggg catcctgcag    1260
ggcaccgaca tcgtcggccc gctcatcgtc taccccctca acaaatccat gtgggacgac    1320
ggcatgtcgg cggcgacgcc gtctgaggac gtgttctacg cggtgtcgct gctcttctcg    1380
tcggtggcgc ccaacgacct ggcgaggctg caggagcaga acaggaggat cctgcgcttc    1440
tgcgacctcg ccgggatcca gtacaagacc tacctggcgc ggcacacgga ccgcagtgac    1500
```

| | |
|---|---|
| tgggtccgcc acttcggcgc cgccaagtgg aatcgcttcg tggagatgaa gaacaagtac | 1560 |
| gaccccaaga ggctgctctc ccccggccag gacatcttca actga | 1605 |

<210> SEQ ID NO 6
<211> LENGTH: 1599
<212> TYPE: DNA
<213> ORGANISM: Saccharomyces cerevisiae

<400> SEQUENCE: 6

| | |
|---|---|
| atgcttttgc aagctttcct tttccttttg gctggttttg cagccaaaat atctgcatca | 60 |
| atgacaaacg aaactagcga tagacctttg gtccacttca cacccaacaa gggctggatg | 120 |
| aatgacccaa atgggttgtg gtacgatgaa aaagatgcca atggcatct gtactttcaa | 180 |
| tacaacccaa atgacaccgt atggggtacg ccattgtttt ggggccatgc tacttccgat | 240 |
| gatttgacta attgggaaga tcaacccatt gctatcgctc ccaagcgtaa cgattcaggt | 300 |
| gctttctctg gctccatggt ggttgattac aacaacacga gtgggttttt caatgatact | 360 |
| attgatccaa gacaaagatg cgttgcgatt tggacttata acactcctga agtgaagag | 420 |
| caatacatta gctattctct tgatggtggt tacactttta ctgaatacca aaagaaccct | 480 |
| gttttagctg ccaactccac tcaattcaga gatccaaagg tgttctggta tgaaccttct | 540 |
| caaaaatgga ttatgacggc tgccaaatca caagactaca aaattgaaat ttactcctct | 600 |
| gatgacttga agtcctggaa gctagaatct gcatttgcca acgaaggttt cttaggctac | 660 |
| caatacgaat gtccaggttt gattgaagtc ccaactgagc aagatccttc caaatcttat | 720 |
| tgggtcatgt ttatttctat caacccaggt gcacctgctg gcggttcctt caaccaatat | 780 |
| tttgttggat ccttcaatgg tactcatttt gaagcgtttg acaatcaatc tagagtggta | 840 |
| gattttggta aggactacta tgccttgcaa actttcttca cactgaccc aacctacggt | 900 |
| tcagcattag gtattgcctg ggcttcaaac tgggagtaca gtgccttgt cccaactaac | 960 |
| ccatggagat catccatgtc tttggtccgc aagtttctt tgaacactga atatcaagct | 1020 |
| aatccagaga ctgaattgat caatttgaaa gccgaaccaa tattgaacat tagtaatgct | 1080 |
| ggtcccctggt ctcgttttgc tactaacaca actctaacta aggccaattc ttacaatgtc | 1140 |
| gatttgagca actcgactgg taccctagag tttgagttgg tttacgctgt taacaccaca | 1200 |
| caaaccatat ccaaatccgt ctttgccgac ttatcacttt ggttcaaggg tttagaagat | 1260 |
| cctgaagaat atttgagaat gggttttgaa gtcagtgctt cttccttctt tttggaccgt | 1320 |
| ggtaactcta aggtcaagtt tgtcaaggag aacccatatt tcacaaacag aatgtctgtc | 1380 |
| aacaaccaac cattcaagtc tgagaacgac ctaagttact ataaagtgta cggcctactg | 1440 |
| gatcaaaaca tcttggaatt gtacttcaac gatggagatg tggtttctac aaatacctac | 1500 |
| ttcatgacca ccggtaacgc tctaggatct gtgaacatga ccactggtgt cgataatttg | 1560 |
| ttctacattg acaagttcca agtaagggaa gtaaaatag | 1599 |

<210> SEQ ID NO 7
<211> LENGTH: 1494
<212> TYPE: DNA
<213> ORGANISM: Saccharomyces cerevisiae

<400> SEQUENCE: 7

| | |
|---|---|
| atgactacgg ataacgctaa ggcgcaactg acctcgtctt caggggtaa cattattgtg | 60 |
| gtgtccaaca ggcttcccgt gacaatcact aaaaacagca gtacgggaca gtacgagtac | 120 |
| gcaatgtcgt ccggagggct ggtcacggcg ttggaagggt tgaagaagac gtacactttc | 180 |

```
aagtggttcg gatggcctgg gctagagatt cctgacgatg agatggatca ggtgaggaag    240
gacttgctgg aaaagtttaa tgccgtaccc atcttcctga gcgatgaaat cgcagactta    300
ctctacaact ggttcagtaa ttctattcta tggccgttat tccattacca tcctggtgag    360
atcaatttcg acgagaatgc gtggttggca tacaacgagg caaaccagac gttcaccaac    420
gagattgcta agactatgaa ccataacgat ttaatctggg tgcatgatta ccatttgatg    480
ttggttccgg aaatgttgag agtcaagatt cacgagaagc aactgcaaaa cgttaaggtc    540
gggtggttcc tgcacacacc attcccttcg agtgaaattt acagaatctt acctgtcaga    600
caagagattt tgaagggtgt tttgagttgt gatttagtcg ggttccactc atacgattat    660
gcaagacatt tcttgtcttc cgtgcaaaga gtgcttaacg tgaacacatt gcctaatggg    720
gtggaatacc agggcagatt cgttaacgta ggggccttcc ctatcggtat cgacgtggac    780
aagttcaccg atgggttgaa aaaggaatcc gtacaaaaga gaatccaaca attgaaggaa    840
actttcaagg gctgcaagat cttagttggt gtcgacaggc tggattacat caaaggtgtg    900
cctcagaagt tgcacgccat ggaagtgttt ctgaacgagc atccagaatg gaggggcaag    960
gttgttctgg tacaggttgc agtgccaagt cgtggagatg tggaagagta ccaatattta   1020
agatctgtgg tcaatgagtt ggtcggtaga atcaacggtc agttcggtac tgtggaattc   1080
gtccccatcc atttcatgca caagtctata ccatttgaag agctgatttc gttatatgct   1140
gtgagcgatg tttgtttggt ctcgtccacc cgtgatggta tgaacttggt ttcctacgaa   1200
tatattgctt gccaagaaga aaagaaaggt tccttaatcc tgagtgagtt cacaggtgcc   1260
gcacaatcct tgaatggtgc tattattgta aatccttgga acaccgatga tctttctgat   1320
gccatcaacg aggccttgac tttgcccgat gtaaagaaag aagttaactg ggaaaaactt   1380
tacaaataca tctctaaata cacttctgcc ttctggggtg aaaatttcgt ccatgaatta   1440
tacagtacat catcaagctc aacaagctcc tctgccacca aaaactgatg aacc         1494
```

<210> SEQ ID NO 8  
<211> LENGTH: 20  
<212> TYPE: DNA  
<213> ORGANISM: Artificial Sequence  
<220> FEATURE:  
<223> OTHER INFORMATION: Synthetic primer

<400> SEQUENCE: 8

```
aacgcctgat tttacgcgag                                                  20
```

<210> SEQ ID NO 9  
<211> LENGTH: 21  
<212> TYPE: DNA  
<213> ORGANISM: Artificial Sequence  
<220> FEATURE:  
<223> OTHER INFORMATION: Synthetic primer

<400> SEQUENCE: 9

```
caataccgca gggcacttat c                                                21
```

<210> SEQ ID NO 10  
<211> LENGTH: 18  
<212> TYPE: DNA  
<213> ORGANISM: Artificial Sequence  
<220> FEATURE:  
<223> OTHER INFORMATION: Synthetic primer

<400> SEQUENCE: 10

```
cccacagatg atgtggac                                                    18
```

```
<210> SEQ ID NO 11
<211> LENGTH: 16
<212> TYPE: DNA
<213> ORGANISM: Artificial Sequence
<220> FEATURE:
<223> OTHER INFORMATION: Synthetic primer

<400> SEQUENCE: 11
gcctgccgca gaccaa                                                          16

<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
caatgcagag ctcagcttca tc                                                   22

<210> SEQ ID NO 13
<211> LENGTH: 25
<212> TYPE: DNA
<213> ORGANISM: Artificial Sequence
<220> FEATURE:
<223> OTHER INFORMATION: Synthetic primer

<400> SEQUENCE: 13
tccagtacgt gcagtccctc ctccc                                                25

<210> SEQ ID NO 14
<211> LENGTH: 19
<212> TYPE: DNA
<213> ORGANISM: Artificial Sequence
<220> FEATURE:
<223> OTHER INFORMATION: Synthetic primer

<400> SEQUENCE: 14
cacgacgggc gttccttgc                                                       19

<210> SEQ ID NO 15
<211> LENGTH: 22
<212> TYPE: DNA
<213> ORGANISM: Artificial Sequence
<220> FEATURE:
<223> OTHER INFORMATION: Synthetic primer

<400> SEQUENCE: 15
ggtggtcgaa tgggcaggta gc                                                   22

<210> SEQ ID NO 16
<211> LENGTH: 23
<212> TYPE: DNA
<213> ORGANISM: Artificial Sequence
<220> FEATURE:
<223> OTHER INFORMATION: Synthetic primer

<400> SEQUENCE: 16
actgaagcgg gaagggactg gct                                                  23
```

DNA CONSTRUCTS AND METHODS TO ENHANCE THE PRODUCTION OF COMMERCIALLY VIABLE TRANSGENIC PLANTS

This application claims the benefit of U.S. Provisional Application No. 60/461,459, filed Apr. 9, 2003, and is a divisional of U.S. application Ser. No. 10/821,711 filed Apr. 8, 2004, issued as U.S. Pat. No. 7,575,917, the disclosure of which is incorporated herein by reference in its entirety.

FIELD OF THE INVENTION

This invention relates to the field of plant molecular biology and plant genetic engineering. Plant genetic engineering methods are used to create novel DNA constructs that contain heterologous genetic elements that when expressed in transgenic plants provide useful phenotypes. More specifically, the invention comprises DNA constructs and methods for using the constructs, such that more transgenic plants that are regenerated from plant cell culture are capable of success as commercial plant candidates.

BACKGROUND OF THE INVENTION

Transformation of plant cells by an *Agrobacterium* mediated method involves exposing plant cells and tissues to a suspension of *Agrobacterium* cells that contain certain DNA plasmids. These DNA plasmids have been specifically constructed to contain transgenes that will express in plant cells (U.S. Pat. No. 5,034,322). Most often, one or more of the transgenes is a positive selectable marker transgene that permits plant cells to grow in the presence of a positive selection compound, for example an antibiotic or herbicide. These cells can be further manipulated to regenerate into whole fertile plants.

The methods for introducing transgenes in plants by an *Agrobacterium* mediated transformation method utilizes a T-DNA (transfer DNA) that incorporates the genetic elements of a transgene and transfers those genetic elements into the genome of a plant. The transgene(s) are constructed in a DNA plasmid vector and are usually bordered by an *Agrobacterium* Ti plasmid right border DNA region (RB) and a left border DNA region (LB). During the process of *Agrobacterium* mediated transformation the DNA plasmid is nicked by VirD2 endonuclease at the right and left border regions and the T-DNA region is inserted into the plant genome. The integration of the T-DNA into the plant genome generally begins at the RB and continues to the end of the T-DNA, at the LB. However, the endonucleases sometimes do not nick equally at both borders. When this happens, the T-DNA that is inserted into the plant genome often contains some or all of the plasmid vector DNA. This phenomenon is referred to as border read-through. It is usually preferred that only the transgene(s) located between the right and left border regions (T-DNA) is transferred into the plant genome without any of the adjacent plasmid vector DNA (vector backbone). The vector backbone DNA contains various plasmid maintenance genetic elements, e.g., origin of replications, bacterial selectable marker genes, and other DNA fragments not desirable in commercial crop products for regulatory issues.

Considerable resources are directed at screening the genome of transgenic crop plants for the presence of the vector-backbone DNA. Methods such as polymerase chain reaction (PCR) and Southern blot analysis are most often employed to identify the extraneous vector backbone DNA. These methods are time consuming and expensive for large scale screening work. Vector backbone DNA can be incorporated by read through of the left border region or may integrate into the plant genome independently of the T-DNA (Kononov, et al., *Plant J.* 11, 945-957, 1997). The transgenic plants that are found to contain the vector backbone DNA are generally not viable for commercialization. Substantial efforts are wasted regenerating plants from plant cell culture that have no commercial potential. It would be useful to have a DNA construct and a method that would greatly reduce the occurrence of vector backbone DNA in the genome of transgenic plants. Fewer transgenic plants would have to be produced if a greater number were free of vector backbone DNA. Hence, fewer assays would have to be performed to confirm that the backbone DNA is absent.

Hanson, et al. (U.S. Pat. No. 6,521,458) describes a DNA construct that contains a lethal gene in the vector backbone that, when expressed, kills the plant cell. However, the control of the expression of lethal gene products in bacteria and plant cells can be problematic. Lethal gene expression must be controlled by various genetic elements to prevent expression in bacteria and in non-target plant cells and tissues. The use of non-lethal negative selectable marker genes for plant cells in the backbone would be a substantial improvement over the use of lethal genes. Non-lethal negative selectable marker genes can provide a visual means to distinguish plant cells and tissues that are expressing the non-lethal negative selectable marker gene products, the selection of the plant cells and plants is more controllable, and plant cells containing the non-lethal negative selectable marker genes are potentially rescuable. The gene used for this purpose can be any gene affecting plant cell division, shoot elongation or producing pleiotropic shoot or leaf phenotypes.

Scorable maker genes for example beta-glucuronidase (GUS) (Kononov, et al., *Plant J.* 11, 945-957, 1997), can provide a means to detect the presence of backbone DNA, but do not provide a means to select against the cells that contain them and the assay is tissue destructive. Negative selectable marker genes that are conditional lethal can also be used in the backbone DNA. Representative examples of other conditional lethal gene products include: *E. coli* guanine phosphoribosyl transferase that converts thioxanthine into toxic thioxanthine monophosphate (Besnard et al., Mol. Cell. Biol. 7:4139-4141, 1987); alkaline phosphatase, which will convert inactive phosphorylated compounds such as mitomycin phosphate and doxorubicin-phosphate to toxic dephosphorylated compounds; fungal (e.g. *Fusarium oxysporum*) or bacterial cytosine deaminase (codA) that will convert 5-fluorocytosine to the toxic compound 5-fluorouracil (Mullen, PNAS 89:33, 1992); carboxypeptidase G2 which will cleave the glutamic acid from para-N-bis(2-chloroethyl) aminobenzoyl glutamic acid, thereby creating a toxic benzoic acid mustard; and Penicillin-V amidase, which will convert phenoxyacetabide derivatives of doxorubicin and melphalan to toxic compounds (see generally, Vrudhula et al., J. of Med. Chem. 36(7):919-923, 1993; Kern et al., Canc. Immun. Immunother. 31(4):202-206, 1990); and phosphonate monoester hydrolase, pehA (U.S. Pat. No. 5,254,801). However, exogenous substrates must be added in order to provide the toxic product that is lethal to the cell containing the backbone DNA. The present invention does not require adding additional substrates to the culture media or exogenously treating the plant culture cells with a substrate as needed for the conditional lethal gene product.

Plant hormone signal transduction genes and hormone biosynthetic pathway genes can be used as selectable marker genes for plant transformation and in a method to produce marker free transgenic plants (U.S. Pat. No. 6,326,192). However, these genes must be removed if the plants are to be further developed as commercially viable plants as described. The genes and compositions illustrated therein can be used in the present invention as non-lethal negative selectable marker genes of the vector backbone DNA.

Gene products that metabolize endogenous plant cell substrates can function as metabolic interference gene of the present invention. For example, a sacB gene, encoding levansucrase and responsible for neutral polyfructan (levan) synthesis using sucrose as a substrate, was identified in many bacteria such as *Bacillus* spp., *Erwinia* spp. etc. Transgenic plants expressing sacB gene aimed at increasing drought resistance or sink strength were previously reported in tobacco, potato, sugar beet, maize and ryegrass (Ebskamp et al. Bio/Technol. 12, 272-275, 1994; van der Meer at al. Plant Cell, 6, 561-570, 1994; Caimi et al. Plant Physiol. 110, 355-363, 1996; Rober et al. Planta, 199, 528-536, 1996; Ye et al. Plant Cell Rep., 20: 205-212, 2001). However, when the vacuole targeted sacB gene driven by CaMV 35S promoter was repeatedly transformed into tobacco and ryegrass, only stunted plants were recovered (Ye et al. 2001). In corn, the sacB expressing kernels disturbed grain filling and resulted in shrunken seeds with very low germination frequency (Caimi et al. 1996). In potato, the expression of the sacB gene in tubers lead to smaller tubers (Rober et al. 1996). These results revealed that expression of the sacB gene severely inhibit plant cell and tissue development.

Other genes encoding metabolic interference enzymes, such as yeast invertase, yeast trehalose-6-phosphate synthase may also be used in same way. It was reported that expression of yeast invertase (Suc2, Carlson et al., Nucleic Acids Res. 11 (6), 1943-1954, 1983) in tobacco and *Arabidopsis* strongly inhibit shoot elongation and root development (Sonnewald et al. Plant J. 1:95-106, 1991), and constitutive expression of yeast trehalose-6-phosphate synthase (TPS1, Bell et al. Eur. J. Biochem. 209 (3), 951-959 (1992) in tobacco exhibited stunted growth and lancet-shape leaves (Romero et al. Planta 201:293-297, 1997). The metabolic interference genes, for example, a polynucleotide encoding a levansucrase, an invertase or a trehalose-6-phosphate synthase are useful as non-lethal negative selectable marker transgenes in the present invention.

The present invention has incorporated a non-lethal negative selectable marker transgene into the vector backbone DNA of a DNA plasmid used to transform plant cells. These transgenes are designed to express a non-lethal gene product in plant cells that contain the vector backbone DNA of the DNA plasmid. The gene products of the non-lethal negative selectable marker transgene are involved in plant hormone biosynthesis pathways, plant hormone substrate diversion, plant hormone degradation, or metabolic interference. The use of these DNA plasmids to transform plant cells provides for enhanced production of commercially viable plants.

SUMMARY OF THE INVENTION

The invention comprises a DNA plasmid comprising an *Agrobacterium* Ti plasmid first border region linked to at least one transgene, the transgene can be a selectable marker gene and additionally an agronomic gene of interest linked to an *Agrobacterium* Ti plasmid second border region linked to a vector backbone DNA, wherein is contained a non-lethal negative selectable marker gene. The non-lethal negative selectable marker gene comprises a plant hormone biosynthetic pathway gene or a metabolic interference gene. The overexpression of the plant hormone biosynthetic pathway gene provides enhanced expression of a plant hormone, or serves to convert a plant hormone substrate into a nonfunctional hormone analog, or to divert the plant hormone substrate into another biosynthetic pathway. The non-lethal negative selectable marker gene can further comprise a plant hormone degradative gene that reduces the amount of an endogenous plant hormone. The non-lethal negative selectable marker gene can further comprise a plant hormone biosynthetic gene or a portion thereof arranged in an antisense orientation that reduces the amount of an endogenous plant hormone by post transcriptional gene suppression. The non-lethal negative selectable marker gene can further comprise a metabolic interference gene that when overexpressed in a plant cell provides an aberrant phenotype. The aberrant phenotype is preferably a reduced growth phenotype or malformation of shoots or leaves.

The DNA plasmid further comprises plant expression cassettes that comprise promoters that function in plant cells. These plant expression cassettes provide plant positive selectable marker genes, genes of agronomic interest, and the non-lethal negative selectable marker genes.

The non-lethal negative selectable marker gene that comprises a plant hormone biosynthetic pathway gene contained in the DNA plasmid is selected from the group consisting of gibberellic acid (GA) pathway genes, cytokinin pathway genes, auxin pathway gene, ethylene pathway genes and abcisic acid pathway genes.

The DNA plasmid of the present invention comprises a non-lethal negative selectable marker gene that diverts substrates of the GA pathway into non-GA active compounds. For example, a transgene of this type encode an enzyme that comprises phytoene synthase, GA 20-oxidase or GA 2β, 3β-hydroxylase. A DNA plasmid may contain a GA degrading enzyme, for example, a GA 2-oxidase.

The DNA plasmid of the present invention comprises a non-lethal negative selectable marker gene that encodes an enzyme in the cytokinin biosynthetic pathway, for example, an isopentenyl transferase (IPT).

The DNA plasmid of the present invention comprises a non-lethal negative selectable marker gene that is an enzyme in the auxin biosynthetic pathway, for example, a plant IAA synthase gene or *Agrobacterium* tumor genes: iaaM, iaaH, rolABC or other tumor or hairy root genes isolated from various *Agrobacterium* species.

The DNA plasmid of the present invention comprises a non-lethal negative selectable marker gene that is an enzyme in the ethylene biosynthetic pathway. For example, a gene encoding an ACC synthase. A DNA plasmid may also contain a gene that encodes for an ethylene degrading enzyme, e.g., ACC deaminase. A DNA plasmid of the present invention may also contain a gene that encodes an ethylene receptor. A DNA plasmid of the present invention may also contain a transgene that encodes a plant hormone signaling protein.

The DNA plasmid of the present invention comprises a non-lethal negative selectable marker gene that is a metabolic interference gene. For example, metabolic interference genes include, but are not limited to sacB gene encoding a levansucrase, a Suc2 gene encoding a yeast invertase, or a TPS1 gene encoding a yeast trehalose-6-phosphate synthase. Metabolic interference genes additionally include those that are constructed to function in a post transcriptional gene suppression mechanism.

The DNA plasmid of the present invention is transformed into an *Agrobacterium* cell for use in a method to transfer to the plant cell transgenes contained in the plasmid. The *Agrobacterium* cell comprises a DNA plasmid comprising an *Agrobacterium* Ti plasmid first border region linked to at least one transgene of agronomic interest linked to an *Agrobacterium Ti plasmid second border region linked to a non-lethal negative selectable marker gene linked to a vector backbone DNA.

The invention provides a method for enhancing the selection of commercially viable transgenic plants comprising the steps of: a) transforming a plurality of plant cells with the DNA plasmid comprising a positive selectable marker gene in the T-DNA and a non-lethal negative selectable marker gene in the plasmid backbone; and b) selecting said plant cells on a positive selection compound; and c) regenerating said selected plant cells into intact plants; wherein the plants are reduced in the occurrence of plasmid backbone DNA and have a lower copy number for the transgene of agronomic interest. The plants produced by the method are an aspect of the invention.

DETAILED DESCRIPTION OF THE INVENTION

Figure 1:
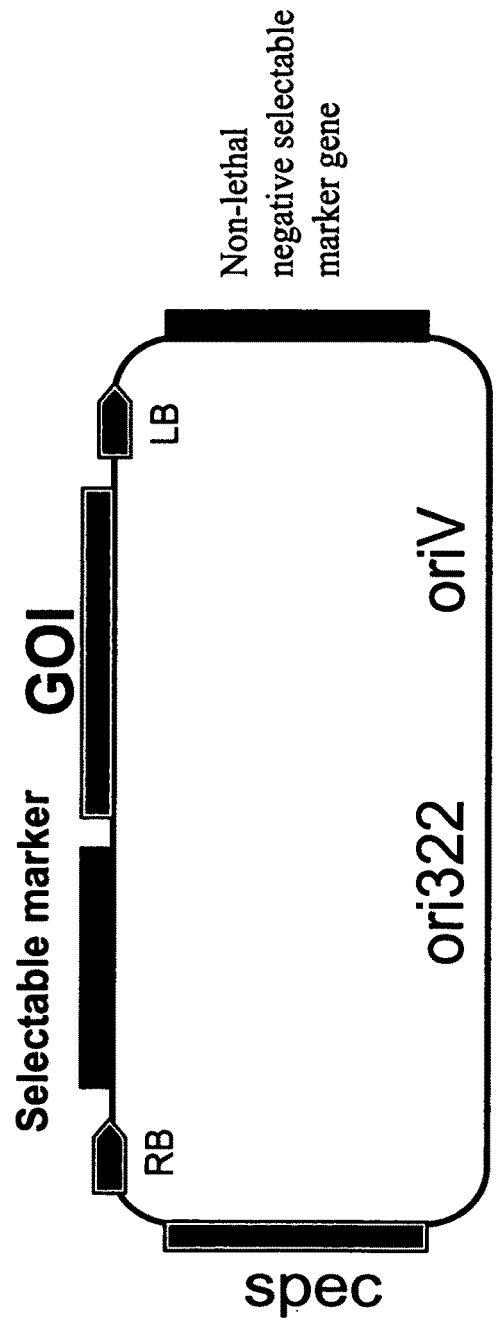
FIG. 1. Schematic illustration of DNA plasmids of the present invention
FIG. 2. Plasmid map of pMON80101
FIG. 3. Plasmid map of pMON77406
FIG. 4. Plasmid map of pLAGILBO1.0033
FIG. 5. Plasmid map of pLAGILBO1.0037
FIG. 6. Plasmid map of pMON69869
FIG. 7. Plasmid map of pMON75157
FIG. 8. Plasmid map of pMON75182
FIG. 9. Plasmid map of pLAGILBO1.0035
FIG. 10. Plasmid map of pLAGILBO1.0038
FIG. 11. Plasmid map of pMON75183
FIG. 12. Plasmid map of pMON75181
FIG. 13. Plasmid map of pMON42066
FIG. 14. Effect of non-lethal selectable marker gene on the backbone frequency of corn plants transformed with pMON75181 (crtB) and pMON75182 (ipt).

The present invention is based, in part, on a DNA plasmid that contains a non-lethal negative selectable marker gene cassette located in a region of the plasmid that is outside of a T-DNA and associated with the plasmid maintenance DNA (vector backbone DNA). The non-lethal negative selectable marker gene contains a gene product that when expressed in a transgenic plant cell is non-lethal, however, interferes with the normal regeneration of the transgenic plant cell into an intact transgenic plant that includes shoot, leaves, and roots. The invention provides a method for use of the DNA plasmid to enhance the selection of plant cells that are for commercial use. The plant cells that are regenerated into intact fertile transgenic plants have enhanced commercial viability due in part to the absence of vector backbone DNA and in part to the reduced copy number of the T-DNA in the plant genome.

Polynucleic Acid Molecules of the Present Invention

The DNA molecules that encode the non-lethal negative selectable marker gene products are identified in the present invention to comprise a polynucleic acid molecule that when expressed in a plant cell is non-lethal to the plant cell, however, interferes with the ability of the plant cell to regenerate into an intact plant at a normal rate or produce an aberrant phenotype compared to plant cells or regenerated plant parts that do not contain the polynucleic acid molecule.

Polynucleic acid molecule as used herein means a deoxyribonucleic acid (DNA) molecule or ribonucleic acid (RNA) molecule. Both DNA and RNA molecules are constructed from nucleotides linked end to end, wherein each of the nucleotides contains a phosphate group, a sugar moiety, and either a purine or a pyrimidine base. Polynucleic acid molecules can be single or double-stranded polymers of nucleotides read from the 5' to the 3' end. Polynucleic acid molecules may also optionally contain synthetic, non-natural or altered nucleotide bases that permit correct read through by a polymerase and do not alter expression of a polypeptide encoded by that polynucleic acid molecule.

The polynucleotide molecule of the present invention is defined by a nucleotide sequence, which as used herein means the linear arrangement of nucleotides to form a polynucleotide of the sense and complementary strands of a polynucleic acid molecule either as individual single strands or in the duplex. As used herein both terms "a coding sequence" and "a structural polynucleotide molecule" mean a polynucleotide molecule that is translated into a polypeptide, usually via mRNA, when placed under the control of appropriate regulatory molecules. The boundaries of the coding sequence are determined by a translation start codon at the 5'-terminus and a translation stop codon at the 3'-terminus. A coding sequence can include, but is not limited to, genomic DNA, cDNA, and recombinant polynucleotide sequences. Homologs, orthologs or paralogs of polynucleotides encoding the non-lethal negative selectable marker gene products used in the present invention can be identified in DNA databases and isolated from the source organism. Alternatively, an artificial DNA molecule encoding the non-lethal negative selectable marker gene products can be designed and created by chemically synthesis using procedures known to those skilled in the art. DNA primers and probes are often synthetic DNA molecules. In addition, full length coding sequences or fragments thereof can be made using synthetic DNA primer molecules using methods known to those skilled in the art.

The polynucleic acid molecules of the present invention may be combined with other non-native, or "heterologous" sequences in a variety of ways. By "heterologous" sequences it is meant any sequence that is not naturally found joined to the nucleotide sequence providing a gene product of the present invention, including, for example, combinations of nucleotide sequences from the same plant that are not naturally found joined together, or the two sequences originate from two different species. The term "operably linked" or "linked", as used herein makes reference to the physical and function arrangement of regulatory and structural polynucleotide molecules that causes regulated expression of an operably linked structural polynucleotide molecule.

The expression of a DNA construct or transgene means the transcription and stable accumulation of sense or antisense RNA or protein derived from the polynucleotide molecule of the present invention or translation thereof. "Sense" RNA means RNA transcript that includes the mRNA and so can be translated into polypeptide or protein by the cell. "Antisense RNA" means a RNA transcript that is complementary to all or part of a target primary transcript or mRNA and that when expressed in a transgenic cell interferes with the expression of a target gene (U.S. Pat. No. 5,107,065). The complementarity of an antisense RNA may be with any part of the specific gene transcript, i.e., at the 5' non-coding sequence, 3' non-translated sequence, introns, or the coding sequence. "RNA transcript" means the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. A polynucleotide molecule of the present invention may comprise an antisense sequence complementary to a host cell target polynucleotide. A polynucleotide molecule of the present invention may also comprise a double stranded RNA product that when expressed in the host cell provides post transcriptional gene suppression of a target host gene The post transcriptional gene suppression by anti-sense oriented RNA to regulate gene expression in plant cells is disclosed in U.S. Pat. No. 5,107,065 and U.S. Pat. No. 5,759,829. Post transcriptional gene suppression by sense-oriented RNA to regulate gene expression in plants is disclosed in U.S. Pat. No. 5,283,184 and U.S. Pat. No. 5,231,020. Post transcriptional gene suppression by double-stranded RNA to suppress genes in plants by RNAi is disclosed in International Publication. WO 99/53050 using recombinant DNA constructs comprising sense-oriented and anti-sense-oriented elements of a targeted gene in separate transcription units or in a single transcription unit. See also International Publication No. WO 99/49029, US Patent Application Publication 2003/0175965 A1 (Lowe et al.), U.S. patent application Ser. No. 10/465,800, and U.S. Pat. No. 6,506,559. Another DNA construct for RNAi gene suppression comprising a singly-oriented gene element bordered by oppositely-oriented promoters is disclosed in U.S. Patent Application Publication 2003/0061626 A1 and U.S. Pat. No. 6,326,193. See also U.S. application Ser. No. 10/393,347, which discloses constructs and methods for simultaneously expressing one or more recombinant genes while simultaneously suppressing one or more native genes in a transgenic plant. See also U.S. Pat. No. 6,448,473, which discloses multigene expression vectors for use in plants. All of the above-described patents, applications and international publications disclosing materials and methods for post transcriptional gene suppression in plants are incorporated herein by reference.

A preferred method of post transcriptional gene suppression in plants employs either sense-oriented or anti-sense-oriented, transcribed RNA which is stabilized, e.g. with a terminal hairpin structure. A preferred DNA construct for effecting post transcriptional gene suppression is transcribed to a segment of anti-sense oriented RNA having homology to a gene targeted for suppression, where the anti-sense RNA segment is followed at the 3' end by a contiguous, complementary, shorter segment of RNA in the sense orientation. The use of self-stabilized anti-sense RNA oligonucleotides in plants is disclosed in International Publication No. 94/01550. See also International Publication No. 98/05770 where the anti-sense RNA is stabilized by hairpin forming repeats of poly (CG) nucleotides. See also U.S. Patent Application Publication 2002/0048814 A1, where sense or anti-sense RNA is stabilized by a poly(T)-poly(A) tail. See also U.S. Patent Application Publication 2003/0018993 A1 where sense or anti-sense RNA is stabilized by an inverted repeat of a sub-sequence of a NOS gene. See also U.S. Patent Application Publication 2003/0036197 A1 (Glassman et al.) where RNA having homology to a target is stabilized by two complementary RNA regions.

Plant cell non-lethal negative selectable marker transgene of the present invention comprise polynucleotides that encode for polypeptides and enzymes related to plant hormones. Plant hormones, that include gibberellins, cytokinins, auxins, ethylene, and abcisic acid can be manipulated to affect the regeneration of plant cells into intact plants.

The overexpression of a class of enzymes that use substrates of the gibberellic acid (GA) biosynthetic pathway, but that do not result in the production of bioactive GA are useful to reduce the amount of substrate available for GA biosynthesis in a plant cell. The GA pathway and description of enzymes and substrates as illustrated in U.S. Patent Publication 2002005309 and WO0009722, and including GA 20-oxidase (U.S. Pat. No. 6,455,675) and GA 2β, 3β-hydroxylase, and phytoene synthase. Phytoene synthase is an enzyme involved in the production of vitamin A (U.S. Pat. No. 5,656,472, US20020051998, US20020092039, U.S. Pat. No. 6,429,356, herein incorporated by reference). The DNA encoding phytoene synthase has been isolated from bacterial and plant sources (U.S. Pat. No. 5,429,939, herein incorporated by reference). The *Erwinia herbicola* phytoene synthase gene (crtB, U.S. Pat. No. 6,429,356) is particularly useful for the production of carotenoid pigments and in the present invention to reduce plant cell regeneration. Fray et al. (The Plant Journal 8:693-701, 1995) showed that constitutive expression of a fruit phytoene synthase gene in transgenic tomatoes causes dwarfism by redirecting metabolites from the gibberellin pathway. The phytoene synthase enzyme as used in the present invention functions to divert the substrate geranylgeranyl pyrophosphate (GGPP) from the gibberellic acid biosynthetic pathway to the carotenoid biosynthic pathway in plant cells containing the vector backbone DNA. The resulting diversion results in a reduced amount of substrate available for the production of GA. The plant cell reduced in GA is delayed in shoot formation during plant regeneration from plant cell tissue culture. Additionally, the plant callus tissue in culture is an orange color due to the overproduction of carotenoid pigments. The present invention provides a DNA construct containing a phytoene synthase gene in the vector backbone that when overexpressed in a plant cell reduces the rate at which the plant cell regenerates into an intact plant, thereby providing a selectable advantage to transgenic plant cells not containing the vector backbone. Other enzymes of the GA biosynthetic pathway that include GGPP synthases (U.S. Pat. No. 6,410,356) are also useful in the present invention. GA 2-oxidase gene sequences, e.g., isolated from bean, *Arabidopsis*, soybean, maize, and cotton (U.S. Pat. No. 6,670,527 and U.S. Patent publication US20020053095, herein incorporated by reference) can be used to reduce GA levels and delay shoot elongation in plant cell culture. A GA 2-oxidase gene product functions by reducing bioactive gibberellin levels. Hydroxylation of bioactive GAs, such as GA1 and GA4, by 2-oxidase renders them inactive, while hydroxylation of biosynthetic precursors, such as GA9 and GA20, creates non-preferable substrates for GA biosynthetic enzymes. Overexpression of the 2-oxidase protein can therefore be used to directly inactivate GA levels or indirectly down-regulate endogenous bioactive GA levels by affecting the substrate levels and hence delaying shoot regeneration. The present invention provides for DNA constructs that contain GA related enzymes, herein described, in which the plant expression cassette containing the polynucleic acid encoding these GA related enzymes occur in the vector backbone DNA.

The transgenic overexpression of enzymes in the cytokinin biosynthetic pathway has been shown to affect the cytokinin levels in plant cells and transgenic plants. For example, isopentenyltransferase (IPT) is an enzyme used in cytokinin synthesis, the gene (ipt) having been isolated from *Agrobacterium tumefaciens* Ti plasmid (Barry et al., Proc. Natl. Acad. Sci. 81:4776-4780, 1984). Isopentenyltransferase uses 5'-AMP and isopentenyl diphosphate to catalyze the formation of isopentenyl-adenosine-5'-monophosphate, the first intermediate in cytokinin biosynthesis. Overexpression of the IPT leads to elevated cytokinin levels in transgenic plants (Medford et al., Plant Cell 1:403-413, 1989). The expression of IPT in a plant cell can induce regeneration of physiologically abnormal shoots from transformed protoplasts or leaf disks. This phenotype can be used as a marker (Ebinuma et al., Proc. Natl. Acad. Sci. 94:2117-2121, 1997). The CKI1 (cytokinin-independent 1) gene expression provides a similar phenotype (Kakimoto, Science 274:982-985, 1996). Increased cytokinin levels have been described to have use as a selectable marker for plant transformation, e.g., inducible control of IPT (U.S. Pat. No. 6,452,068, and U.S. Pat. No. 6,326,192, both herein incorporated by reference) and inducible control of ESR-2 (U.S. Pat. No. 6,441,276, herein incorporated by reference) and ESR1-A (U.S. Pat. No. 6,407,312, herein incorporated by reference). In the present invention, the cytokinin biosynthesis related proteins are preferably constitutively expressed. These genes when used in the DNA plasmid constructs of the present invention as components of the vector backbone, induce abnormal non-embryogenic callus formation in monocot cells that contain the vector backbone. The DNA plasmids of the present invention are especially useful for monocot cell transformation as few embryos are produced that contain the backbone DNA. When used to transform dicot plant cells, the cells containing the chimeric cytokinin biosynthetic genes produce abnormal shoots that fail to produce abundant roots. Additionally, enzymes that degrade cytokinin, e.g., cytokinin oxidase (U.S. Pat. No. 6,229,066, herein incorporated by reference) can be used in the present invention to serve as a non-lethal negative selectable marker transgene for plant cells that contain the vector backbone.

Auxin, such as indole-3-acetic acid (IAA), affects plant cell growth and development especially when in combination with other plant hormones. Variations of the cytokinin/auxin concentration ratio cause the enhancement in plant growth to occur preferentially in certain tissues. For example, a high cytokinin/auxin ratio promotes growth of shoots, whereas a low cytokinin to auxin ratio promotes the growth of roots (Depicker et al. (1983) in *Genetic Engineering of Plants*, T. Kosunge, C. P. Meredith and A. Hollaender, eds., Plenum Press, New York, p. 154). Attempts to increase the endogenous synthesis of IAA have involved the genetic engineering of plants to contain bacterial genes for the biosynthesis of IAA. These include the *Agrobacterium* sp. IAA biosynthetic pathway genes: iaaM, iaaH, rolABC or other tumor or hairy root genes isolated from *Agrobacterium* species that function to provide auxin molecules.

Generally transgenic plants expressing higher levels of IAA via bacterial enzymes showed phenotypic abnormalities (Klee et al. Genes Devel. 1:86-96, 1987; Schmulling et al. EMBO J. 7:2621-2629, 1988). Such transgenic plants exhibited higher than normal levels of both IAA conjugates and of free IAA, particularly when the bacterial iaaM (tryptophan monooxygenase) and/or iaaH (indolacetamide hydrolase) genes were linked to powerful heterologous promoters (Sitbon, F. (1992) Transgenic Plants Overproducing IAA—A Model System to Study Regulation of IAA Metabolism, Swedish University of Agricultural Sciences, Umea, Sweden). The biosynthesis of conjugates of IAA in *Zea mays* is catalyzed by UDP-glucose:indol-3-ylacetyl-glucosyl transferase (EC 2.4.1.121; also called IAA-Glucose Synthetase, IAGlu Synthetase, IAGlu Transferase; U.S. Pat. Nos. 5,919, 998, and 6,489,541, both herein incorporated by reference). Overexpressing of this enzyme causes aberrant growth of cells in tissue culture. The present invention contemplates the use of auxin biosynthetic genes in the vector backbone to provide a distinctive phenotype to plant cells containing the vector backbone DNA of the DNA plasmids.

Ethylene biosynthesis has been established, methionine is converted to ethylene with S-adenylmethionine (SAM) and 1-aminocyclopropane-1-carboxylic acid (ACC) as intermediates. The production of ACC from SAM is catalyzed by the ACC synthase enzyme. ACC synthase is produced in ripening fruits and stressed plants and is encoded by a highly divergent gene family (U.S. Pat. No. 5,723,766, herein incorporated by reference). The conversion of ACC to ethylene is catalyzed by ethylene forming enzyme (EFE), (Spanu et al., EMBO J. 1991, 10, 2007. For example, 1-aminocyclopropane-1-carboxylic acid synthase (ACS) and ethylene-forming enzyme (EFE) genes isolated as described in U.S. Pat. No. 5,886,164, herein incorporated by reference. ACC oxidase, which converts ACC to ethylene, is expressed constitutively in most tissues (Yang et al., Ann. Rev. Plant Physiol. 1984, 35, 155), but is induced during fruit ripening (Gray et al. Cell 1993 72, 427), DNA and protein compositions of ACC oxidase or homologs thereof are useful as disclosed in U.S. Pat. No. 6,043,409, herein incorporated by reference. The DNA constructs of the present invention contemplates the presence of a plant expression cassette in the vector backbone that provides overexpression of ethylene biosynthetic enzymes in plant cells that contain the vector backbone DNA. An ACC deaminase enzyme metabolizes ACC by converting it to alpha-ketobutyrate and ammonia (U.S. Pat. No. 5,702,933, herein incorporated by reference). Plants transformed to express the ACC deaminase enzyme have reduced levels of ethylene in their tissues. Transformed plants have been modified with an ethylene insensitive receptor ETR-1 are characterized by a decrease in ethylene response as compared to a plant not containing insensitive receptor (U.S. Pat. No. 5,689, 055, herein incorporated by reference). The DNA constructs of the present invention contemplates the presence of a plant expression cassette in the vector backbone that provides overexpression of ethylene degradative enzymes or ethylene insensitive receptor proteins in plant cells that contain the vector backbone DNA.

The plant hormone abscisic acid (ABA) is thought to play a role during late embryogenesis, mainly in the maturation stage by inhibiting germination during embryogenesis (In *Abscisic Acid: Physiology and Biochemistry*, W. J. Davies and H. G. Jones, eds. (Oxford: Bios Scientific Publishers Ltd.), pp. 99-124, 1991). Mutations that effect seed development and are ABA insensitive have been identified in *Arabidopsis* and maize. The ABA insensitive (abi3) mutant of *Arabidopsis* and the viviparous1 (vp1) mutant of maize are detected mainly during late embryogenesis (McCarty, et al., Plant Cell 1, 523-532, 1989, and Parcy et al., Plant Cell 6, 1567-1582, 1994). Both the VP1 gene and the ABI3 genes have been isolated and were found to share conserved regions (Giraudat, J. Current Opinion in Cell Biology 7:232-238, 1995, and McCarty, D. R. Annu. Rev. Plant Physiol. Plant Mol. Biol. 46:71-93, 1995). The VP1 gene has been shown to function as a transcription activator (McCarty, et al., Cell 66:895-906, 1991). It has been suggested that ABI3 has a similar function. LEC1 genes and related mutant molecules described in U.S. Pat. No. 6,320,102 (herein incorporated by reference), i.e., lec2, fus3-3 and abi3-3 that cause similar defects in late embryogenesis to those of lec1-1 or lec1-2. These mutants are desiccation intolerant, sometimes viviparous and have activated shoot apical meristems. The lec2 and fus3-3 mutants are sensitive to ABA and possess trichomes on their cotyledons and therefore can be categorized as leafy cotyledon-type mutants. The abi3-3 mutants belong to a different class of late embryo defective mutations that are insensitive to ABA and do not have trichomes on the cotyledons. The DNA constructs of the present invention contemplates the presence of a plant expression cassette in the vector backbone that provides overexpression of ABA related proteins in plant cells that contain the vector backbone DNA, thereby providing a means to distinguish in tissue culture plant cell with and without vector backbone.

The Bas1 gene in *Arabidopsis* encodes a cytochrome P450 (CYP72B1), which has a role in brassinosteroid signaling or synthesis. Overexpression of the Bas1 gene in plants causes a dark green, dwarf phenotype which mimics plants that have low levels of the plant hormone, brassinolide (U.S. Patent Publication US20020073446, herein incorporated by reference). This gene and other related plant hormone signaling gene products may be used in the present invention to provide an aberrant phenotype to the plants containing the vector backbone DNA segment comprising these genes as the non-lethal negative selectable marker transgene.

Metabolic interference genes include coding sequences that encode for a protein that has catalytic activity on an endogenous plant cell substrate, yet is non-lethal to the cell. The substrate includes, but is not limited to, simple sugars, fatty acids, amino acids, or nucleotides. Therefore, metabolic interference genes encode, for example, biosynthetic pathway enzymes, enzymes that divert substrates from the pathways, enzymes that degrade or inactivate substrates of the pathways, or gene products that affect the expression of pathway enzymes, these can include antisense RNA molecules or transcription enhancers and repressors. More specifically, examples of metabolic interference proteins include, but are not limited to levansucrase, invertase, and trehalose synthase. The metabolic interference gene expression alters the normal occurrence or distribution of the substrate in the plant cell. The result is a cell that is reduced in cell division, cell elongation, or regeneration into a plant. A metabolic interference gene can comprise an antisense sequence complementary to an endogenous plant cell gene or transcript that when expressed in a plant cell results in reduced plant cell division, cell elongation, or regeneration into a plant. The DNA constructs of the present invention contemplates the presence of a plant expression cassette in the vector backbone that provides overexpression of metabolic interference enzymes or an antisense RNA that functions as a repressive molecule of metabolic processes in plant cells that contain the vector backbone DNA. The DNA construct may be made to provide an antisense RNA that forms a double stranded RNA molecule when expressed in plant cells and provides for post transcriptional gene suppression of a target host gene.

A gene generally refers to a segment of DNA that is involved in producing a polypeptide. Such segment of DNA includes regulatory molecules preceding (5' non-coding DNA molecules) and following (3' non-coding DNA molecules) the coding region, as well as intervening sequences (introns) between individual coding segments (exons). A "native gene" means a gene as found in nature with its own regulatory DNA sequences. "Chimeric gene" means any gene that is not a native gene, comprising heterologous regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "transgene" is a gene that has been introduced into the genome by a transformation procedure resulting in a transgenic organism. A transgene may also be constructed to produce a gene product that does not encode for a polypeptide, for example, an antisense RNA.

Genetic regulatory sequences are components of the gene and when linked as a transgene include polynucleotide molecules located upstream (5' non-coding sequences), within, or downstream (3' non-translated sequences) of a structural polynucleotide sequence, and that influence the transcription, RNA processing or stability, or translation of the associated structural polynucleotide sequence. Regulatory sequences may include promoters, translation leader sequences (e.g., U.S. Pat. No. 5,659,122), introns (e.g., U.S. Pat. No. 5,424,412), and polyadenylation recognition sequences.

The DNA construct of the present invention can, in one embodiment, contain a promoter that causes the overexpression of the transgene product of the present invention, where "overexpression" means the expression of the product either not normally present in the host cell, or present in said host cell at a higher level than that normally expressed from the endogenous gene encoding said polypeptide. Promoters, which can cause the overexpression of the transgene product of the present invention, are generally known in the art, e.g., viral promoters (P-CaMV35S, U.S. Pat. No. 5,352,605; P-FMV35S, U.S. Pat. Nos. 5,378,619 and 5,018,100), and various plant derived promoters, e.g., plant actin promoters (P-Os.Act1, U.S. Pat. Nos. 5,641,876 and 6,429,357). These promoters are examples of constitutive promoters that generally express in most tissues of the plant. Other constitutive promoters are know in the art of plant molecular biology and are useful in the present invention.

The expression level or pattern of the promoter of the DNA construct of the present invention may be modified to enhance its expression. Methods known to those of skill in the art can be used to insert enhancing elements (for example, subdomains of the CaMV35S promoter, Benfey et al., EMBO J. 9: 1677-1684, 1990) into the 5' sequence of genes. In one embodiment, enhancing elements may be added to create a promoter, which encompasses the temporal and spatial expression of the native promoter of the gene of the present invention but have quantitatively higher levels of expression. Similarly, tissue specific expression of the promoter can be accomplished through modifications of the 5' region of the promoter with elements determined to specifically activate or repress gene expression (for example, pollen specific elements, Eyal et al., 1995 Plant Cell 7: 373-384). The term "promoter sequence" or "promoter" means a polynucleotide molecule that is capable of, when located in cis to a structural polynucleotide sequence encoding a polypeptide, functions in a way that directs expression of one or more mRNA molecules that encodes the polypeptide. Such promoter regions are typically found upstream of the trinucleotide, ATG, at the start site of a polypeptide coding region. Promoter molecules can also include DNA sequences from which transcription of transfer RNA (tRNA) or ribosomal RNA (rRNA) sequences are initiated. Transcription involves the synthesis of a RNA chain representing one strand of a DNA duplex. The sequence of DNA required for the transcription termination reaction is called the 3' transcription termination region.

It is preferred that the particular promoter selected should be capable of causing sufficient expression to result in the production of an effective amount of a product to cause the desired phenotype. In addition to promoters that are known to cause transcription of DNA in plant cells, other promoters may be identified for use in the current invention by screening a plant cDNA library for genes that are selectively or preferably expressed in the target tissues and then determine the promoter regions. Promoters that express the linked non-lethal negative selectable maker gene product during the plant tissue culture process to regenerate a plant cell into a plant are especially useful in the present invention.

Promoters that can be used to express transgenes in plants can be derived from genes encoding embryonic storage proteins, which includes the gene encoding the 2S storage protein from *Brassica napus* (Dasgupta et al., Gene 133:301-302, 1993); the 2S seed storage protein gene family from *Arabidopsis*; the gene encoding oleosin 20 kD (kilodalton) from *Brassica napus* (GenBank M63985); the genes encoding oleosin A (GenBank U09118) and oleosin B (GenBank U09119) from soybean; the gene encoding oleosin from *Arabidopsis* (GenBank Z17657); the gene encoding oleosin 18 kD from maize (GenBank J05212, Lee, Plant Mol. Biol. 26:1981-1987, 1994) and the gene encoding low molecular weight sulphur rich protein from soybean (Choi et al., Mol. Gen. Genet. 246:266-268, 1995), can be used in chimeric transgenes. Promoters derived from zein encoding genes (including the 15 kD, 16 kD, 19 kD, 22 kD, 27 kD, and gamma genes, Pedersen et al., Cell 29:1015-1026, 1982) can be used in chimeric transgenes. The zeins are a group of storage proteins found in maize endosperm. Promoters that express in seed tissue are herein referred to as P-Seed, unless otherwise identified.

It is recognized that additional promoters that may be utilized are described, for example, in U.S. Pat. Nos. 5,378,619, 5,391,725, 5,428,147, 5,447,858, 5,608,144, 5,608,144, 5,614,399, 5,633,441, 5,633,435, and 4,633,436, all of which are herein incorporated in their entirety. It is further recognized that the exact boundaries of regulatory sequences may not be completely defined and that DNA fragments of different lengths may have identical promoter activity. Those of skill in the art can identify promoters in addition those herein described that function in the present invention to provide expression of a plant cell non-lethal negative selectable marker transgene polynucleotide molecule.

The translation leader sequence is a DNA genetic element means located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences include maize and petunia heat shock protein leaders (U.S. Pat. No. 5,362,865, herein incorporated by reference), plant virus coat protein leaders, plant rubisco gene leaders, among others (Turner and Foster, Molecular Biotechnology 3:225, 1995).

Transit peptides generally refer to peptide molecules that when linked to a protein of interest directs the protein to a particular tissue, cell, subcellular location, or cell organelle. Examples include, but are not limited to, chloroplast transit peptides, nuclear targeting signals, and vacuolar signals. The chloroplast transit peptide is of particular utility in the present invention to direct expression of the phytoene synthase enzyme to the chloroplast. Chloroplast transit peptides (CTPs) are engineered to be fused to the N terminus proteins to be targeted into the plant chloroplast. Many chloroplast-localized proteins are expressed from nuclear genes as precursors and are targeted to the chloroplast by a chloroplast transit peptide (CTP) that is removed during the import steps. Examples of chloroplast proteins include the small subunit of ribulose-1,5,-bisphosphate carboxylase (RbcS2, rubisco), ferredoxin, ferredoxin oxidoreductase, the light-harvesting complex protein I and protein II, and thioredoxin F. It has been demonstrated in vivo and in vitro that non-chloroplast proteins may be targeted to the chloroplast by use of protein fusions with a CTP and that a CTP sequence is sufficient to target a protein to the chloroplast. Incorporation of a suitable chloroplast transit peptide, such as, the *Arabidopsis thaliana* EPSPS CTP (Klee et al., Mol. Gen. Genet. 210:437-442, 1987), and the *Petunia hybrida* EPSPS CTP (della-Cioppa et al., Proc. Natl. Acad. Sci. USA 83:6873-6877, 1986) has been shown to target heterologous protein to chloroplasts in transgenic plants. The expression of a phytoene synthase enzyme in transgenic plants is targeted to the chloroplast by the addition of a CTP (WO 9714807, U.S. Pat. No. 6,429,356, herein incorporated by reference). Those skilled in the art will recognize that various chimeric constructs can be made that utilize the functionality of a particular CTP to import phytoene synthase or other non-lethal negative selective marker gene products into the plant cell chloroplast as needed.

The 3' non-translated sequences or 3' termination region means DNA sequences located downstream of a structural nucleotide sequence and include sequences encoding polyadenylation and other regulatory signals capable of affecting transcription, mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA. An example of the polyadenylation sequence is the nopaline synthase 3' sequence (nos 3'; Fraley et al., Proc. Natl. Acad. Sci. USA 80: 4803-4807, 1983). The use of different 3' non-translated sequences is exemplified by Ingelbrecht et al., (Plant Cell 1:671-680, 1989).

The laboratory procedures in recombinant DNA technology used herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, 2nd. ed., Cold Spring Harbor Laboratory, Cold Spring Harbor, N.Y. (1989), herein referred to as Sambrook et al., (1989).

Plant Recombinant DNA Constructs and Transformed Plants

The isolated polynucleic acid molecules of the present invention can find particular use in creating transgenic crop plants in which polypeptides of the present invention are overexpressed. Overexpression of these polypeptides in a plant cell can reduce the rate at which a plant cell regenerates into an intact plant or produces a phenotype easily discernable by eye without the addition of exogenous substrates. The DNA plasmid of the present invention can be transformed into a transgenic crop plant cell.

A transgenic crop plant contains an exogenous polynucleotide molecule inserted into the genome of a crop plant cell. A crop plant cell, includes without limitation a plant cell further comprising suspension cultures, embryos, meristematic regions, callus tissue, leaves, roots, shoots, gametophytes, sporophytes, ovules, pollen and microspores, and seeds, and fruit. By "exogenous" it is meant that a polynucleotide molecule originates from outside the plant that the polynucleotide molecule is introduced. An exogenous polynucleotide molecule can have a naturally occurring or non-naturally occurring nucleotide sequence. One skilled in the art understands that an exogenous polynucleotide molecule can be a heterologous molecule derived from a different species than the plant into which the polynucleotide molecule is introduced or can be a polynucleotide molecule derived from the same plant species as the plant into which it is introduced. The exogenous polynucleotide (transgene) when expressed in a transgenic plant can provide an agronomically important trait. The transgenes of agronomic interest (GOI) provide beneficial agronomic traits to crop plants, for example, including, but not limited to genetic elements comprising herbicide resistance (U.S. Pat. No. 5,633,435; U.S. Pat. No. 5,463,175), increased yield (U.S. Pat. No. 5,716,837), insect control (U.S. Pat. No. 6,063,597; U.S. Pat. No. 6,063,756; U.S. Pat. No. 6,093,695; U.S. Pat. No. 5,942,664; U.S. Pat. No. 6,110,464), fungal disease resistance (U.S. Pat. No. 5,516,671; U.S. Pat. No. 5,773,696; U.S. Pat. No. 6,121,436; and U.S. Pat. No. 6,316,407, and U.S. Pat. No. 6,506,962), virus resistance (U.S. Pat. No. 5,304,730 and U.S. Pat. No. 6,013,864), nematode resistance (U.S. Pat. No. 6,228,992), bacterial disease resistance (U.S. Pat. No. 5,516,671), starch production (U.S. Pat. No. 5,750,876 and U.S. Pat. No. 6,476, 295), modified oils production (U.S. Pat. No. 6,444,876), high oil production (U.S. Pat. No. 5,608,149 and U.S. Pat. No. 6,476,295), modified fatty acid content (U.S. Pat. No. 6,537, 750), high protein production (U.S. Pat. No. 6,380,466), fruit ripening (U.S. Pat. No. 5,512,466), enhanced animal and human nutrition (U.S. Pat. No. 5,985,605 and U.S. Pat. No. 6,171,640), biopolymers (U.S. Pat. No. 5,958,745 and U.S. Patent Pub US20030028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689, 041), and biofuel production (U.S. Pat. No. 5,998,700), the genetic elements and transgenes described in the patents listed above are herein incorporated by reference.

The present invention also provides a plant recombinant DNA construct for producing transgenic crop plants. Methods that are well known to those skilled in the art may be used to prepare the crop plant recombinant DNA construct of the present invention. These methods include in vitro recombinant DNA techniques, synthetic techniques, and in vivo genetic recombination. Such techniques are described in Sambrook et al., (1989). Exogenous polynucleotide molecules created by the methods may be transferred into a crop plant cell by *Agrobacterium* mediated transformation or other methods known to those skilled in the art of plant transformation.

The DNA constructs are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA (transfer DNA), that along with transfer molecules provided by the *Agrobacterium* cells, permits the integration of the T-DNA into the genome of a plant cell. The DNA constructs also contain the vector backbone DNA segments that provide replication function and antibiotic selection in bacterial cells, for example, an *E. coli* origin of replication such as ori322, a broad host range origin of replication such as Ec.oriV or oriRi, and a coding region for a selectable marker such as Spec/Strp that encodes for Tn7 aminoglycoside adenyltransferase (aad4) conferring resistance to spectinomycin or streptomycin, or a gentamicin (Gm, Gent) selectable marker gene. For plant transformation, the host bacterial strain is often, *Agrobacterium tumefaciens* ABI, C58, or LBA4404, however, other strains known to those skilled in the art of plant transformation can function in the present invention. The present invention provides DNA constructs that contain a plant expression cassette in the vector backbone, that when expressed in a plant cell produces a non-lethal product that preferably reduces the efficient regeneration of the plant cell into a whole intact plant or produces a plant or part thereof that has an aberrant phenotype.

A T-DNA of the DNA construct of the present invention will typically comprise one or more transgenes of agronomic interest and a positive selectable marker that confers a selectable phenotype on plant cells. The marker may provide resistance to a positive selection compound, for example, antibiotic resistance (e.g, kanamycin, G418, bleomycin, hygromycin, etc.), or herbicide resistance (e.g., include but are not limited to: glyphosate, glufosinate, sulfonylureas, imidazolinones, bromoxynil, delapon, cyclohezanedione, protoporphyrionogen oxidase inhibitors, and isoxasflutole herbicides). Polynucleotide molecules encoding proteins involved in herbicide tolerance are known in the art, and include, but are not limited to a polynucleotide molecule encoding 5-enolpyruvylshikimate-3-phosphate synthase (EPSPS, described in U.S. Pat. Nos. 5,627,061, 5,633,435, 6,040,497; Padgette et al. *Herbicide Resistant Crops*, Lewis Publishers, 53-85, 1996; and Penaloza-Vazquez, et al. Plant Cell Reports 14:482-487, 1995; and aroA (U.S. Pat. No. 5,094,945) for glyphosate tolerance; bromoxynil nitrilase (Bxn) for Bromoxynil tolerance (U.S. Pat. No. 4,810,648); phytoene desaturase (crtI, Misawa et al, (1993) *Plant J.* 4:833-840, and (1994) *Plant J.* 6:481-489); for tolerance to norflurazon, acetohydroxyacid synthase (AHAS, aka ALS, Sathasiivan et al. Nucl. Acids Res. 18:2188-2193, 1990); and the bar gene for tolerance to glufosinate and bialaphos (DeBlock, et al. EMBO J. 6:2513-2519, 1987).

In addition to a selectable marker, it may be desirable to use a reporter gene. In some instances a reporter gene may be used with or without a selectable marker. Reporter genes are genes that are typically not present in the recipient organism or tissue and typically encode for proteins resulting in some phenotypic change or enzymatic property. Examples of such genes are provided in Wising et al. Ann. Rev. Genetics, 22, 421 (1988), that is incorporated herein by reference. Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (Biochem. Soc. Trans. 15, 17-19, 1987) to identify transformed cells, referred to herein as GUS.

The DNA construct of the present invention may be introduced into the genome of a desired plant host by a suitable *Agrobacterium* mediated plant transformation method. Suitable plant transformation plasmid constructs for the purpose of *Agrobacterium* mediated transformation include those derived from a Ti plasmid of *Agrobacterium tumefaciens*, as well as those disclosed, e.g., by Herrera-Estrella et al., (Nature 303:209, 1983); Bevan, (Nucleic Acids Res. 12: 8711-8721, 1984); Klee et al., (Bio-Technology 3:637-642, 1985). Methods for transforming plants by *Agrobacterium tumefaciens*-mediated transformation include: Fraley et al., (Bio/Technology 3:629-635, 1985), and Rogers et al., (Methods Enzymol. 153:253-277, 1987). *Agrobacterium*-mediated transformation is achieved through the use of a genetically engineered soil bacterium belonging to the genus *Agrobacterium*. Several *Agrobacterium* species mediate the transfer of a specific DNA known as "T-DNA", that can be genetically engineered to carry any desired piece of DNA into many plant species. The major events marking the process of T-DNA mediated pathogenesis are induction of virulence genes, and processing and transfer of T-DNA. This process is the subject of many reviews (Ream. Ann. Rev. Phytopathol. 27: 583-618, 1989; Howard and Citovsky, Bioassays, 12:103-108, 1990; Kado, Crit. Rev. Plant Sci. 10:1-32, 1991; Winnans, Microbiol. Rev. 56: 12-31, 1992; Zambryski, Ann. Rev. Plant Physiol. Plant Mol. Biol., 43: 465-490, 1992; Gelvin, In *Transgenic Plants*, S. D. Kung and R. Wu eds., Academic Press, San Diego, pp. 49-87, 1993; Binns and Howitz, In *Bacterial Pathogenesis of Plants and Animals* (Dang, J. L., ed.). Berlin: Stringer Verlag, pp. 119-138, 1994; Hooykaas and Beijersbergen, Ann. Rev. Phytopathol. 32:157-179, 1994; Lessl and Lanka, Cell 77:321-324, 1994; Zupan and Zambryski, Ann. Rev. Phytopathol. 27, 583-618, 1995).

Plant cell regeneration techniques rely on manipulation of certain phytohormones in a tissue culture growth medium, also typically relying on a biocide and/or herbicide marker that has been introduced together with the desired nucleotide sequences. Choice of methodology with suitable protocols being available for hosts from Leguminoseae (alfalfa, soybean, clover, etc.), Umbelliferae (carrot, celery, parsnip), Cruciferae (cabbage, radish, canola/rapeseed, etc.), Cucurbitaceae (melons and cucumber), Gramineae (wheat, barley, rice, maize, etc.), Solanaceae (potato, tobacco, tomato, peppers), various floral crops, such as sunflower, and nut-bearing trees, such as almonds, cashews, walnuts, and pecans. See, for example, Ammirato et al., Handbook of Plant Cell Culture—Crop Species. Macmillan Publ. Co. (1984); Shimamoto et al., Nature 338:274-276 (1989); Fromm, UCLA Symposium on Molecular Strategies for Crop Improvement, Apr. 16-22, 1990. Keystone, Colo. (1990); Vasil et al., Bio/Technology 8:429-434 (1990); Vasil et al., Bio/Technology 10:667-674 (1992); Hayashimoto, Plant Physiol. 93:857-863 (1990); and Datta et al., Bio-technology 8:736-740 (1990). Such regeneration techniques are described generally in Klee et al., Ann. Rev. Plant Phys. 38:467-486 (1987). Methods and compositions for transforming plants by introducing a transgenic DNA construct into a plant genome in the practice of this invention can include any of the well-known and demonstrated methods. For example, *Agrobacterium*-mediated transformation as illustrated in U.S. Pat. Nos. 5,824,877; 5,591,616; and 6,384,301, all of which are incorporated herein by reference.

Plants that can be made by practice of the present invention include, but are not limited to, *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, cilantro, citrus, clementines, coffee, corn, cotton, cucumber, Douglas fir, eggplant, endive, escarole, eucalyptus, fennel, figs, forest trees, gourd, grape, grapefruit, honey dew, jicama, kiwifruit, lettuce, leeks, lemon, lime, Loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini.

The following examples are provided to better elucidate the practice of the present invention and should not be interpreted in any way to limit the scope of the present invention. Those skilled in the art will recognize that various modifications, additions, substitutions, truncations, etc., can be made to the methods and genes described herein while not departing from the spirit and scope of the present invention.

EXAMPLES

Example 1

DNA Plasmids

The DNA plasmids of the present invention are DNA constructs that contain a T-DNA segment and a vector backbone segment. The T-DNA is flanked by *Agrobacterium* Ti plasmid border regions [the right border (RB) and left border (LB) regions] and contains positive selectable marker genes and agronomic genes of interest (GOI). The vector backbone segment contains the non-lethal negative selectable marker gene and the plasmid maintenance elements. DNA plasmids used as controls for comparative purposes contain identical or similar T-DNA expression cassettes, but do not contain the non-lethal negative selectable marker gene in the vector backbone. The basic design of a plasmid of the present invention is illustrated in FIG. 1. In this illustration, the RB and LB elements flank a T-DNA, these border elements may be substituted with other like elements or fragments of related DNA molecules that function as nick sites for an endonucleases provided by the virulence genes of *Agrobacterium*. The selectable marker gene can be selected from any number of genes known to provide plant cell resistance to positive selection compounds such as, antibiotics, e.g., kanamycin, hygromycin, gentamycin, or herbicides, e.g., glyphosate, glufosinate, sulfonylureas, imidazolinones, bromoxynil, delapon, cyclohezanedione, protoporphyrionogen oxidase inhibitors, and isoxaflutole herbicides. The agronomic genes of interest can be selected to provide any number of useful traits to plants. The present invention provides examples of agronomic genes of interest in DNA constructs that include, but are not limited to a herbicide tolerance gene, insect resistance genes, and a yield enhancing gene.

Figure 2:
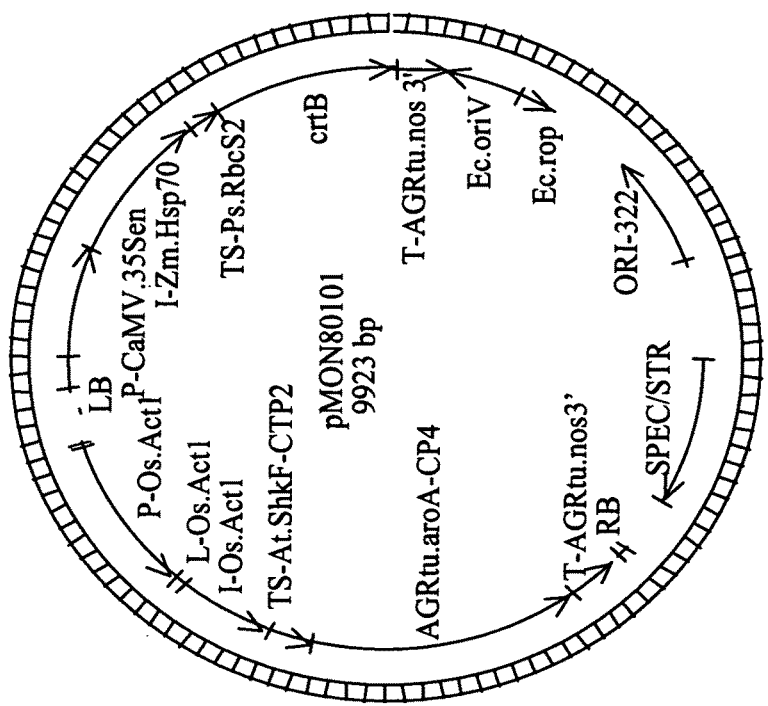

A DNA construct especially useful for expression in monocot plant cells contains the crtB DNA coding sequence with a linked rubisco subunit chloroplast transit peptide leader (SSU, TS-Ps.RbcS2, SEQ ID NO: 1 of U.S. Pat. No. 6,429, 356, herein incorporated by reference) is operably linked to a strong constitutive promoter (P-CaMV.35Sen, U.S. Pat. No. 5,359,142, CaMV 35S promoter with duplicated enhancer) and maize Hsp70 intron (I-Zm.DnaK, U.S. Pat. No. 5,593, 874) and a 3' termination region isolated from the *Agrobacterium tumefaciens* nopaline synthase gene (T-AGRtu.nos 3') as illustrated in pMON80101 (FIG. 2), this expression cassette is located in the vector backbone DNA segment. In pMON80101, the T-DNA contains a plant expression cassette that is both a selectable marker and an agronomic gene of interest (glyphosate tolerance). This expression cassette comprises the promoter, leader, and intron from rice actin1 (P-Os. Act1, U.S. Pat. No. 5,641,876), linked to the chloroplast transit peptide (CTP2) isolated from the *Arabidopsis* ShkF gene, linked to the aroA-CP4 coding sequence from *Agrobacterium tumefaciens* (U.S. Pat. No. 5,633,435), linked to the 3' termination region isolated from the nopaline synthase gene of *Agrobacterium tumefaciens*.

Figure 3:
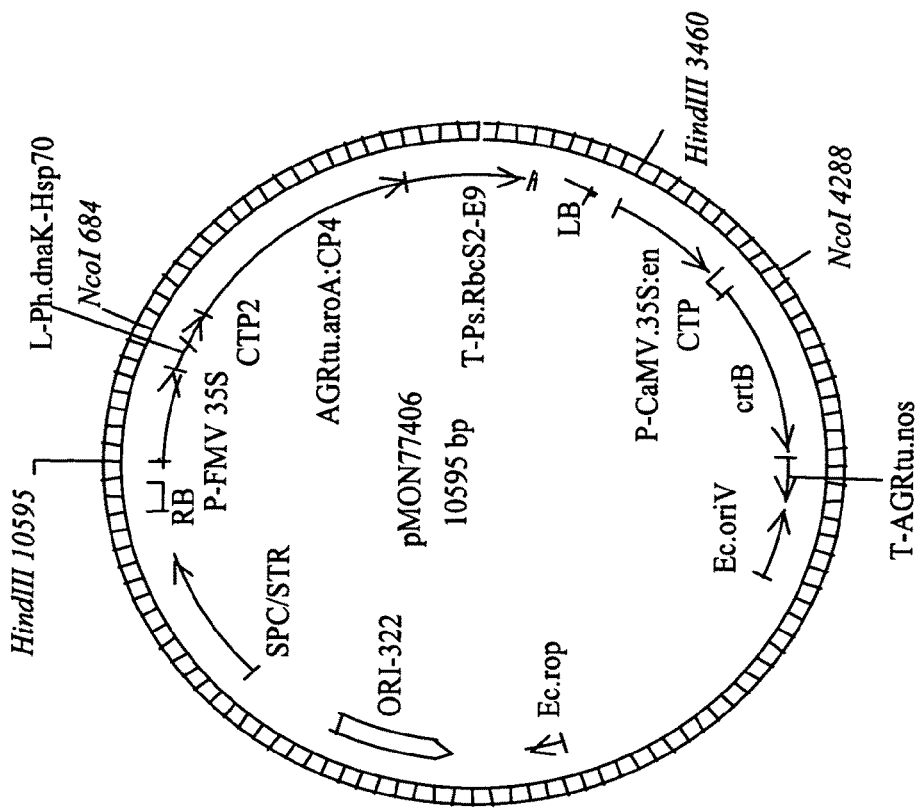

A DNA construct containing the crtB coding sequence encoding a phytoene synthase (SEQ ID NO: 1 of the present invention, or other DNA molecules encoding a phytoene synthase, for example SEQ ID NO: 1 of U.S. Pat. No. 6,429,356) is constructed that is particularly useful for expression in dicot plant cells is illustrated in pMON77406 (FIG. 3). The P-CaMV.35S:en promoter is a strong constitutive promoter that directs expression of the crtB gene product in plant cells. This construct contains the selectable marker gene (P-FMV35S/L-Ph-Hsp70/CTP2-aroA-CP4/T-RbcS2-E9) expression cassette that provides strong constitutive expression of a glyphosate resistant EPSPS enzyme (aroA-CP4). The P-FMV promoter (U.S. Pat. No. 5,378,619), the translation leader isolated from *Petunia hybrida* Hsp70 gene (U.S. Pat. No. 5,362,865), the chloroplast transit peptide (CTP2) isolated from *Arabidopsis* EPSPS operably linked to the aroA-CP4 glyphosate resistant EPSPS coding sequence and linked to the pea rubisco small subunit 3' termination region also referred to as E9. Additional expression cassettes (transgenes of agronomic interest) may be added within the T-DNA to provide enhanced agronomic phenotypes to the transgenic plants containing the T-DNA.

Figure 4:
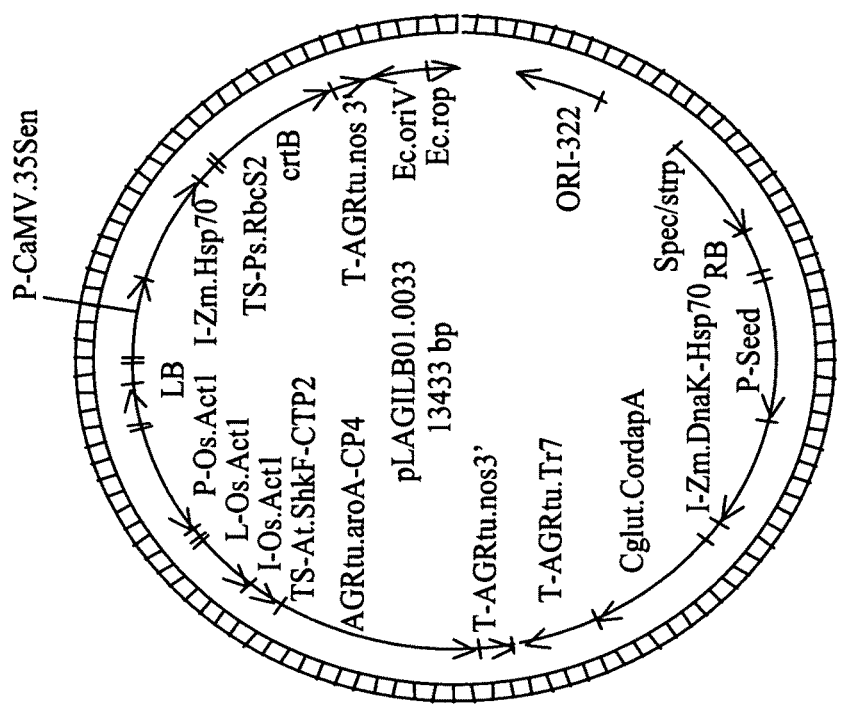

A DNA construct illustrated in FIG. 4 (pLAGILB01.0033) contains a yield enhancing transgene (P-Seed/I-Zm.DnaK-Hsp70/Cglut.CordapA/T-AGRtu.Tr7) and the glyphosate selectable marker gene. The P-Seed promoter functions to provide expression in seed tissues linked to the maize Hsp70 intron. The CordapA gene (*Corynebacterium* dapA, Bonnassie et al. Nucleic Acids Res. 18:6421, 1990) encodes a DHDPS enzyme that is insensitive to lysine inhibition. The transcription termination region is from the Tr7 gene of *Agrobacterium tumefaciens*. The crtB non-lethal negative selectable maker transgene is located in the vector backbone DNA.

Figure 5:
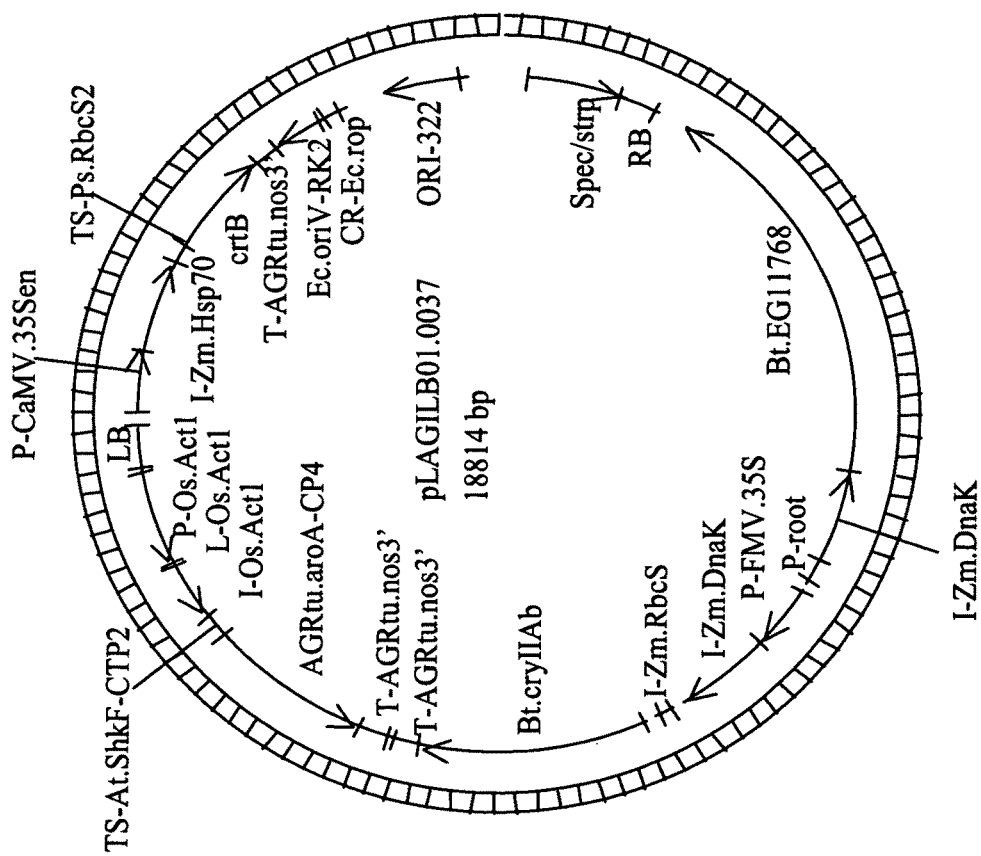

A DNA construct illustrated in FIG. 5 (pLAGILB01.0037) contains two insect resistance transgenes, the polynucleotides of which encode a Bt.EG11768 protein (U.S. Pat. No. 6,242,241) and a Bt.cryIIAb protein (U.S. Pat. No. 6,489,542). The crtB gene is in the backbone DNA, its expression driven by the P-CaMV.35Sen promoter.

Figure 6:
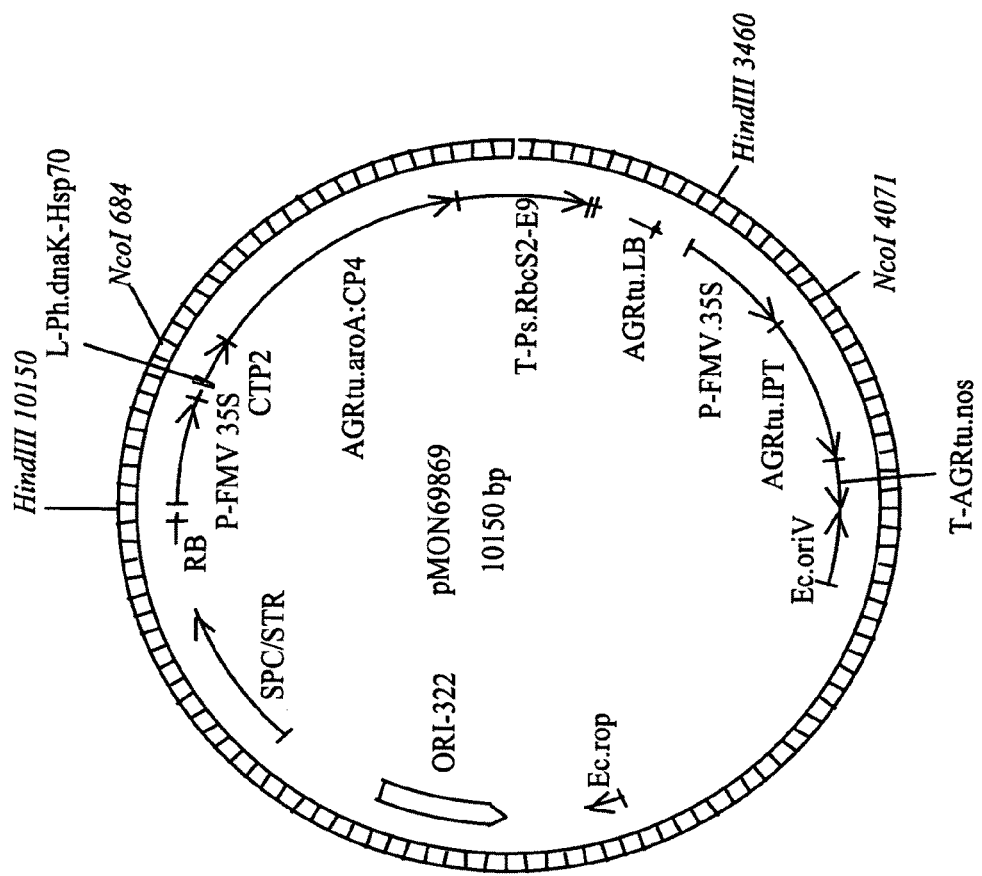
Figure 7:
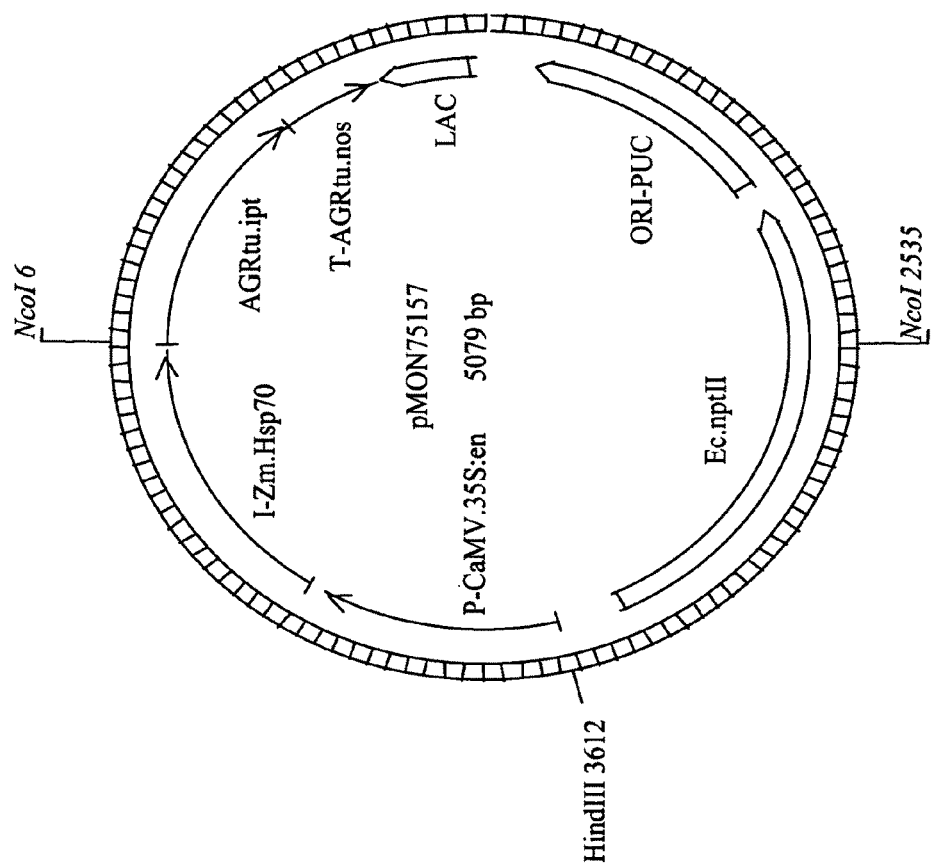

A DNA construct illustrated in FIG. 6 (pMON69869) contains the genetic elements for expression of the selectable marker aroA:CP4 that provides glyphosate resistance, and in the vector backbone DNA, a non-lethal negative selectable marker transgene, the polynucleotide encoding the IPT enzyme from *Agrobacterium tumefaciens* (ipt or AGRtu.ipt, SEQ ID NO:2). A DNA construct illustrated in FIG. 7 (pMON75157) shows a plasmid that contains additional genetic elements useful for expression of the AGRtu.ipt coding sequence. This expression cassette can be used in the vector backbone of DNA plasmids used for *Agrobacterium*-mediated transformation of plant cells.

Figure 8:
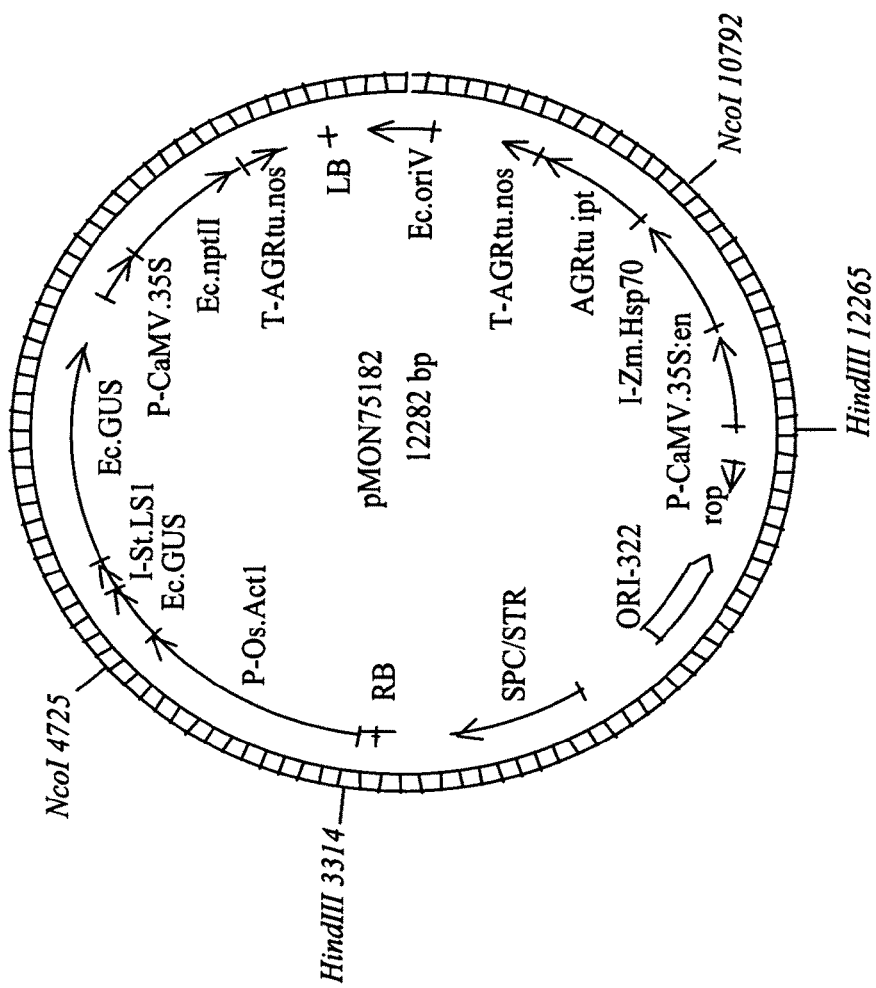

A DNA construct illustrated in FIG. 8 (pMON75182) contains in the T-DNA, the transgenes for a scorable marker gene (GUS) and a positive selectable marker gene (AGRtu.nptII). The AGRtu.ipt coding sequence is contained in the vector backbone DNA. The scorable marker gene may be substituted with transgenes of agronomic interest (GOI) to provide valuable agronomic traits to crop plants.

Figure 9:
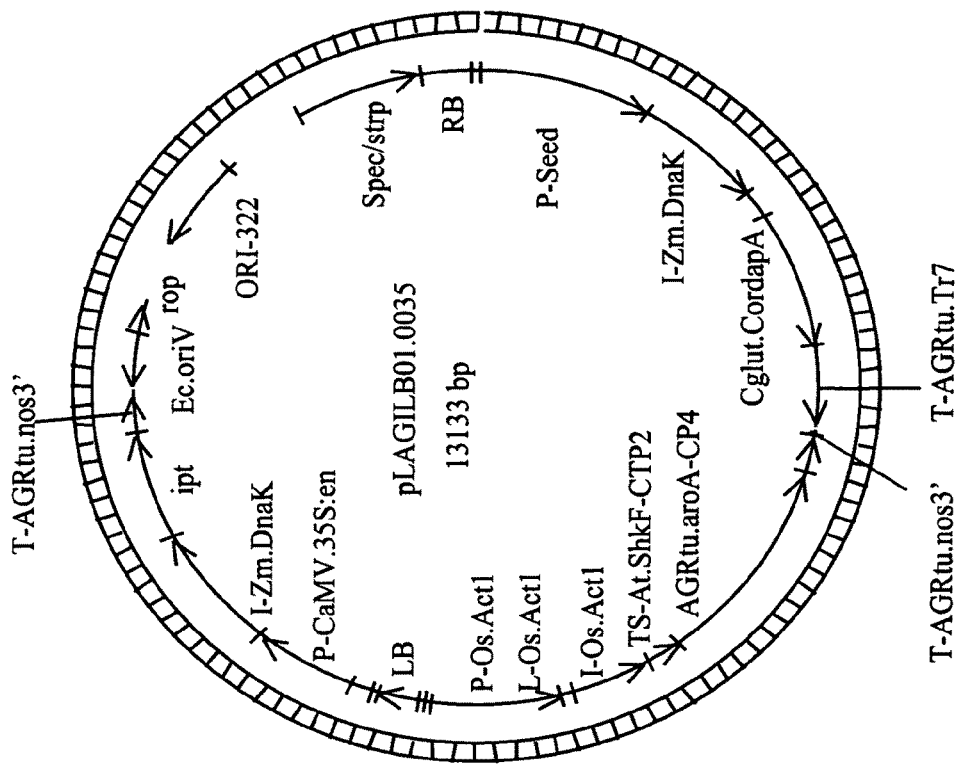

A DNA construct illustrated in FIG. 9 (pLAGILB01.0035) contains in the T-DNA, the transgene for a yield enhancing transgene (P-Seed/I-Zm.DnaK-Hsp70/Cglut.CordapA/T-AGRtu.Tr7) and a glyphosate selectable marker transgene. The ipt expression cassette (P-CaMV.35S:en/I-Zm.DNAK/ipt/T-AGRtu.nos3') is contained in the vector backbone DNA.

Figure 10:
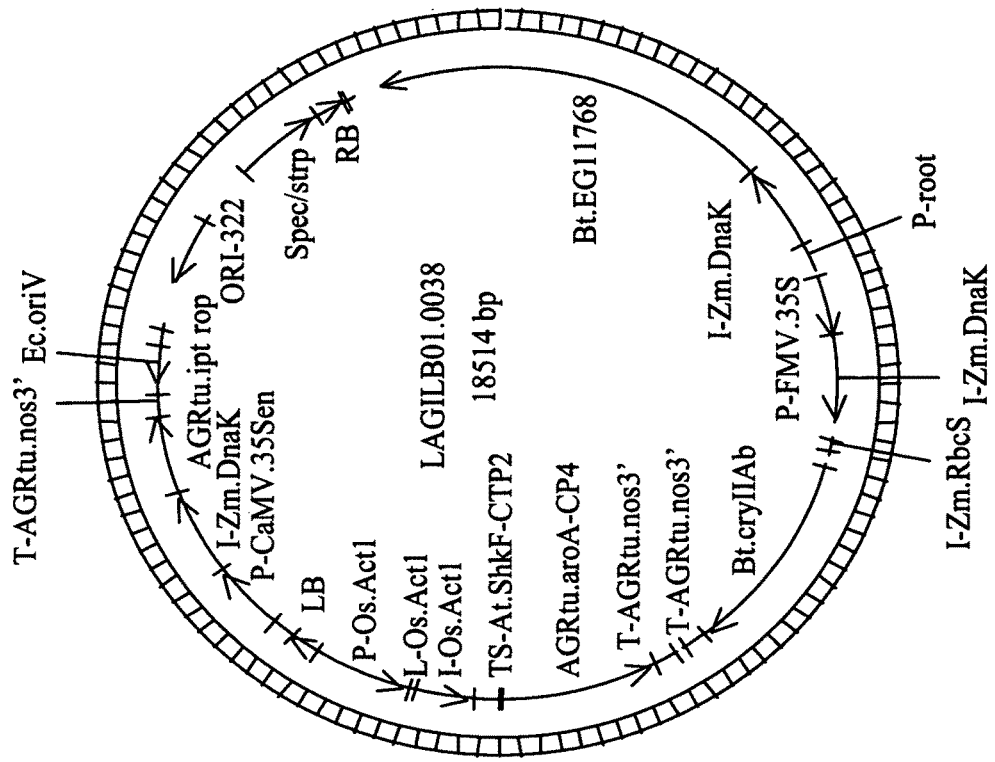

A DNA construct illustrated in FIG. 10 (pLAGILBO1.0038) contains two insect resistance transgenes, the polynucleotides of which encode a Bt.EG11768 protein and a Bt.cryIIAb protein. The AGRtu.ipt gene is in the backbone DNA, the expression driven by the P-CaMV.35Sen promoter.

Figure 11:
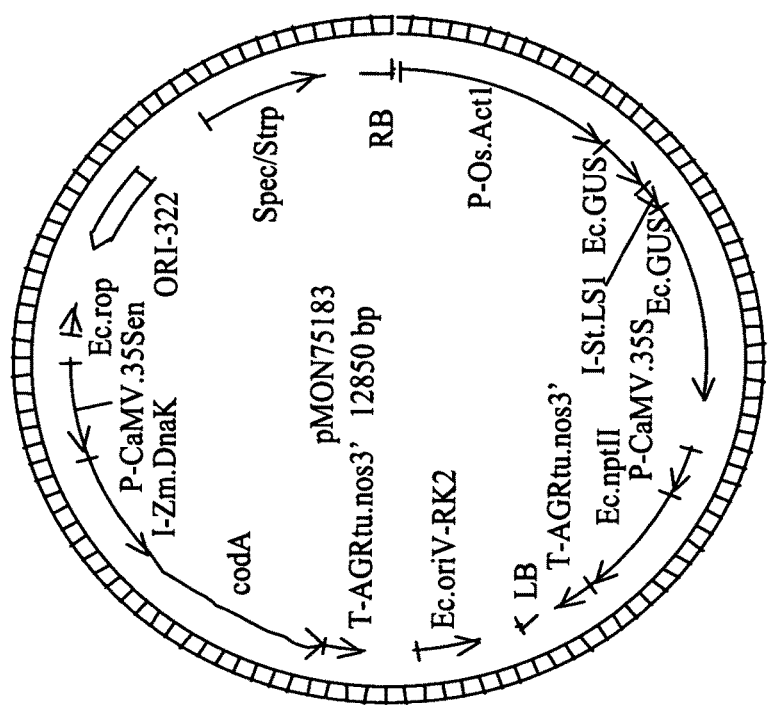

A DNA construct illustrated in FIG. 11 (pMON75183) contains in the T-DNA, the transgenes for a scorable marker gene (GUS) and a positive selectable marker gene (AGRtu.nptII). The coda coding sequence is contained in the vector backbone DNA. The codA provides a conditional lethal selectable marker. During plant cell regeneration, the callus tissue is transferred to media containing 5-fluorocytosine, plant cells that express cytosine deaminase will be killed, leaving only plant cells that do not contain the vector backbone DNA. The scorable marker gene may be substituted with transgenes of agronomic interest (GOI) to provide valuable agronomic traits to crop plants.

Figure 12:
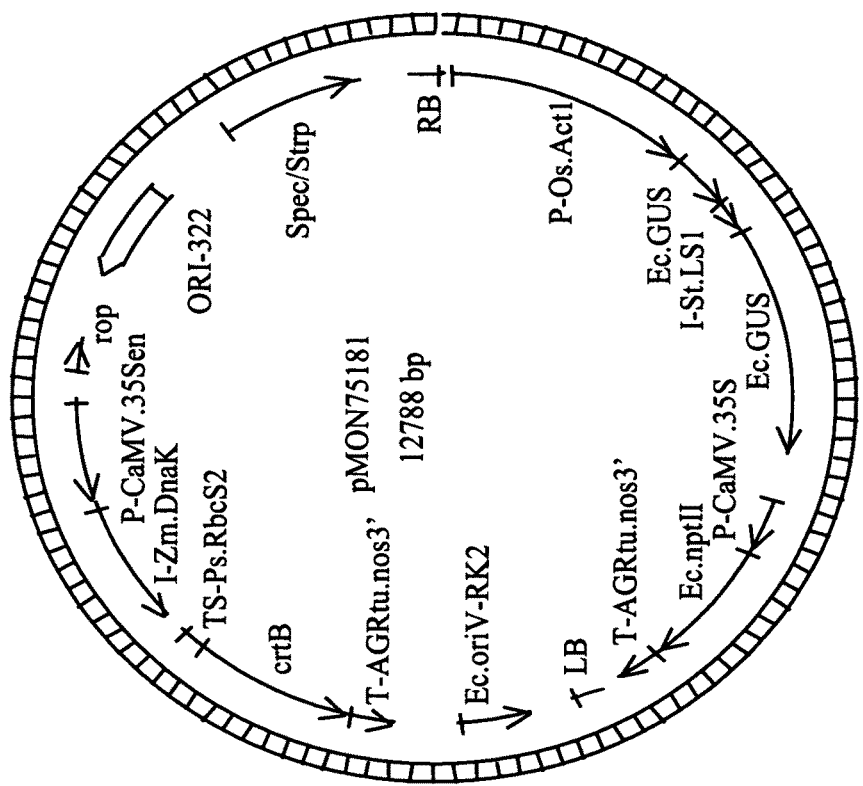

A DNA construct illustrated in FIG. 12 (pMON75181) contains in the T-DNA, the transgenes for a scorable marker gene (GUS) and a positive selectable marker gene (AGRtu.nptII). The T-DNA contains the same expression cassettes as pMON75183. The crtB non-lethal negative selectable maker gene is located in the vector backbone DNA.

Figure 13:
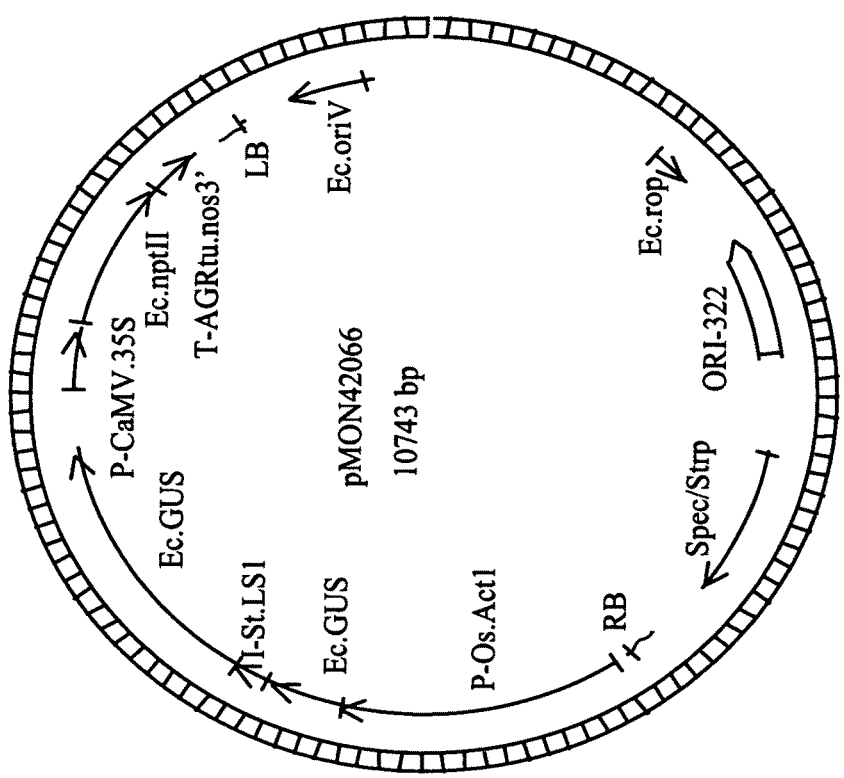

A DNA construct illustrated in FIG. 13 (pMON42066) contains in the T-DNA, the transgenes for a scorable marker gene (GUS) and a positive selectable marker gene (AGRtu.nptII). The T-DNA contains the same expression cassettes as pMON75183 and pMON75181. There is no plant cell non-lethal negative selectable marker (no gene) in the vector backbone DNA.

Figure 16:
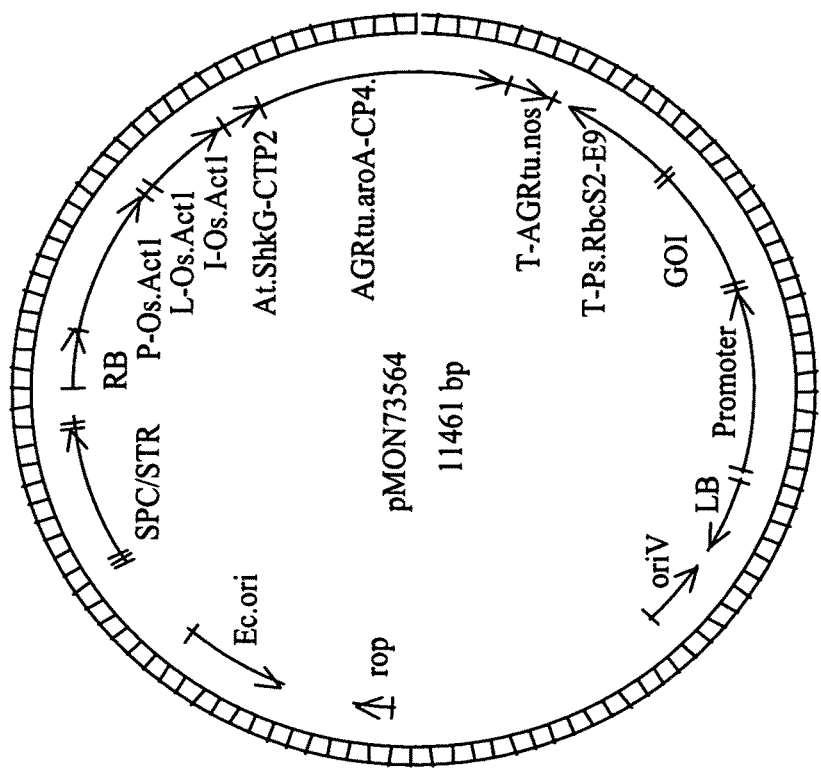
FIG. 16. Plasmid map of pMON73564
FIG. 17. Plasmid map of pMON73565
FIG. 18. Effect of non-lethal selectable marker gene on the backbone frequency of corn plants transformed with pMON73565 (crtB+).

A DNA construct illustrated in FIG. 16 (pMON73564) contains in the T-DNA, the transgenes for a positive selectable marker gene (AGRtu.aroA-CP4) and an expression cassette comprising a promoter and gene of interest. There is no plant cell non-lethal negative selectable marker (no gene) in the vector backbone DNA.

Figure 17:
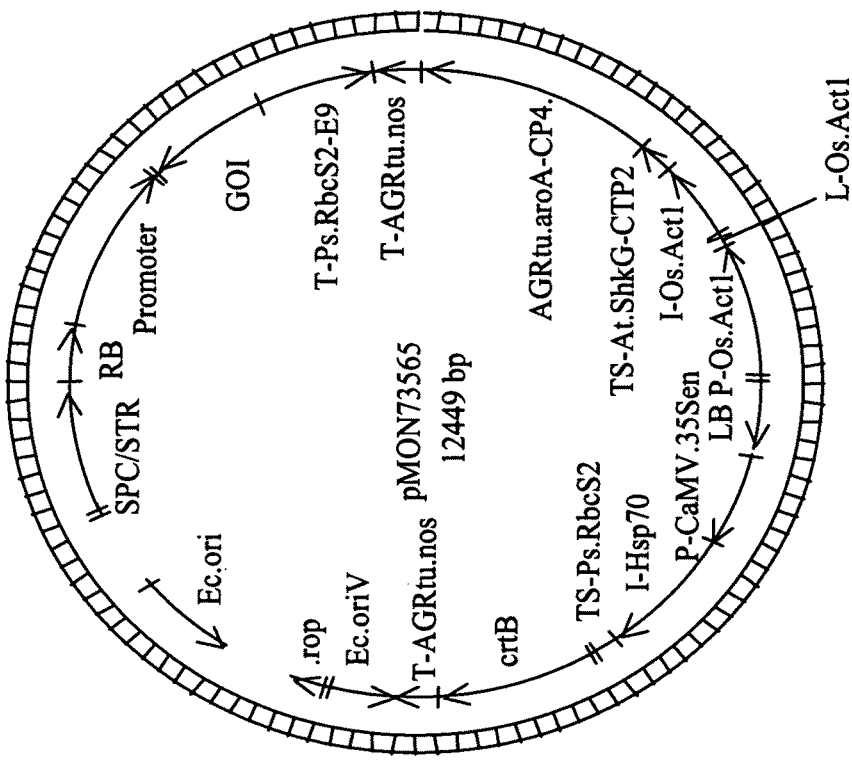

A DNA construct illustrated in FIG. 17 (pMON73565) contains in the T-DNA, the transgenes for a positive selectable marker gene (AGRtu.aroA-CP4) and an expression cassette comprising a promoter and gene of interest. The crtB non-lethal negative selectable maker gene is located in the vector backbone DNA.

Figure 20:
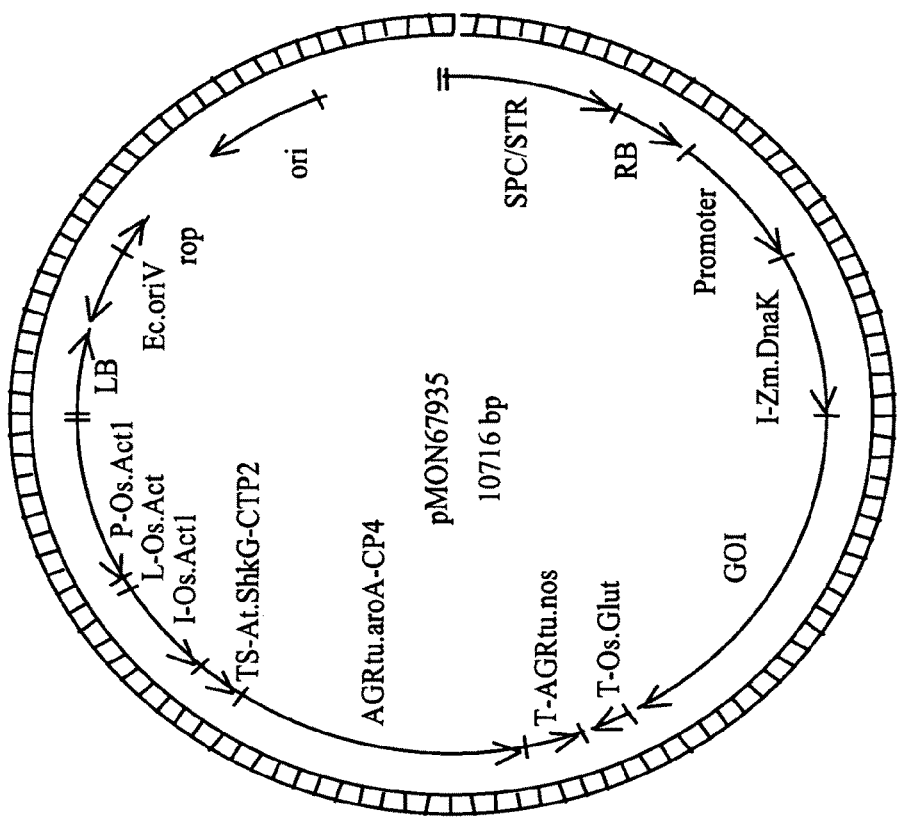
FIG. 20. Plasmid map of pMON67935
FIG. 21. Plasmid map of pMON67936
FIG. 22. Effect of non-lethal selectable marker gene on the backbone frequency of corn plant transformed with pMON67936 (crtB+).

A DNA construct illustrated in FIG. 20 (pMON67935) contains in the T-DNA, the transgenes for a positive selectable marker gene (AGRtu.aroA-CP4) and an expression cassette comprising a promoter and gene of interest. There is no plant cell non-lethal negative selectable marker (no gene) in the vector backbone DNA.

Figure 21:
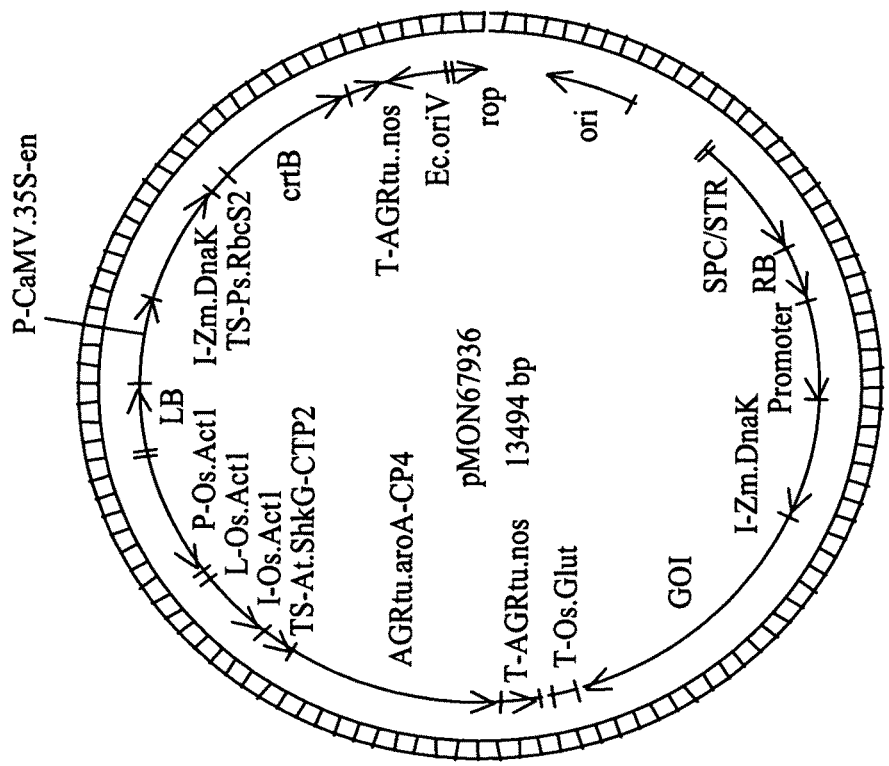

A DNA construct illustrated in FIG. 21 (pMON67936) contains in the T-DNA, the transgenes for a positive selectable marker gene (AGRtu.aroA-CP4) and an expression cassette comprising a promoter and gene of interest. The crtB non-lethal negative selectable maker transgene is located in the vector backbone DNA.

Figure 24:
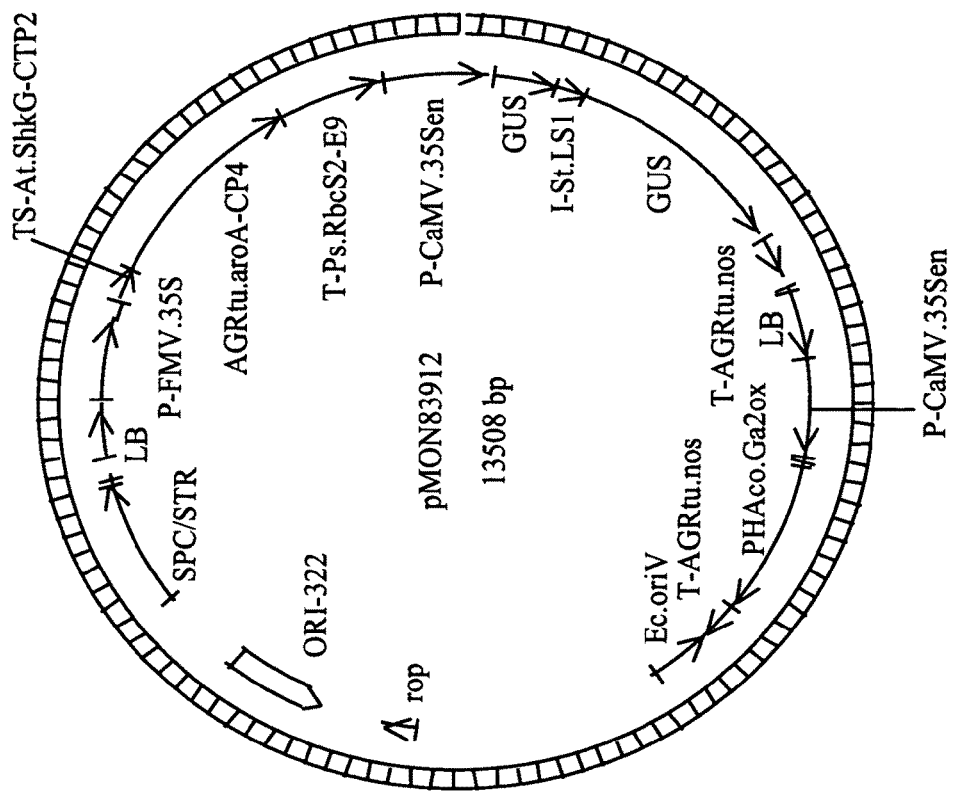
FIG. 24. Plasmid map of pMON83912
FIG. 25. Plasmid map of pMON83908
FIG. 26. Plasmid map of pMON83907

A DNA construct illustrated in FIG. 24 (pMON83912) contains in the T-DNA, the transgenes for a positive selectable marker gene (AGRtu.aroA-CP4) and an expression cassette comprising a GUS reporter gene. A plant cell expression cassette containing the non-lethal negative selectable marker gene encoding a *Phaseolus coccineus* gibberellin 2-oxidase (SEQ ID NO:3) is in the vector backbone DNA.

Figure 25:
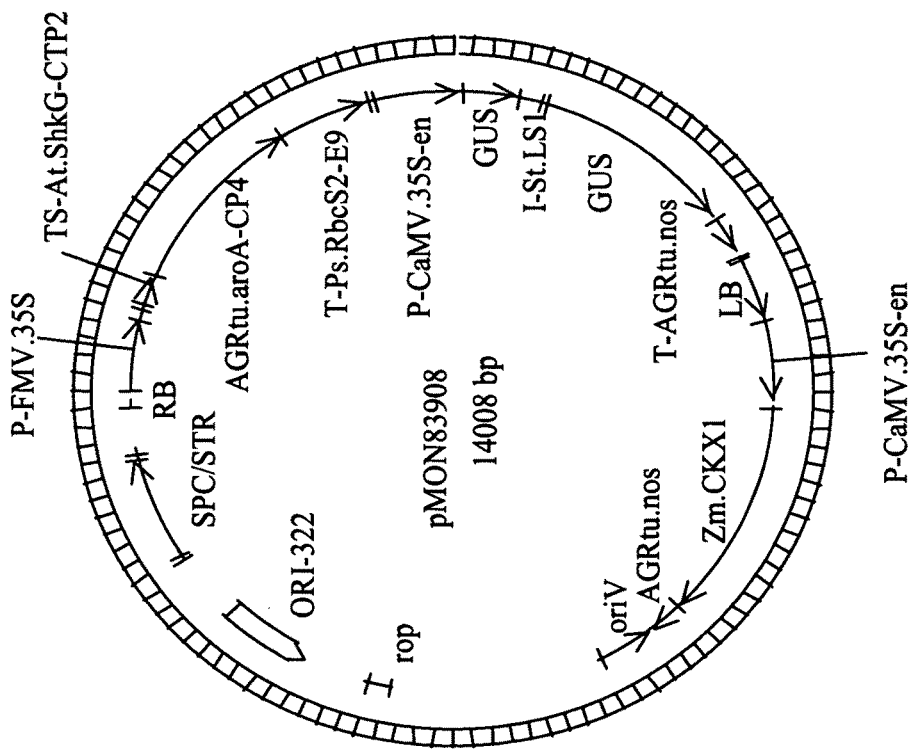
Figure 26:
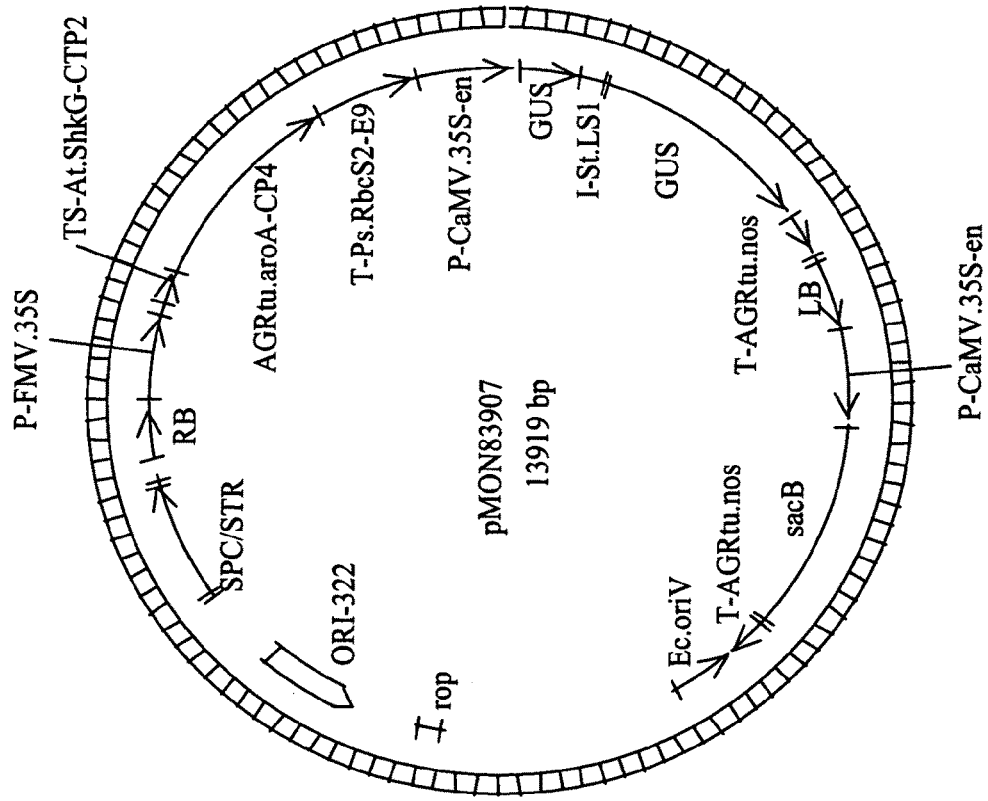

A DNA construct illustrated in FIG. 25 (pMON83908) contains in the T-DNA, the transgenes for a positive selectable marker gene (AGRtu.aroA-CP4) and an expression cassette comprising a GUS reporter gene. A plant cell expression cassette containing the non-lethal negative selectable marker gene (CKX1, SEQ ID NO:4) encoding a cytokinin oxidase is in the vector backbone DNA.

A DNA construct illustrated in FIG. 25 (pMON83907) contains in the T-DNA, the transgenes for a positive selectable marker gene (AGRtu.aroA-CP4) and an expression cassette comprising a GUS reporter gene. A plant cell expression cassette containing the non lethal negative selectable marker gene (sacB, SEQ ID NO:5) encoding a levansucrase is in the vector backbone DNA.

DNA constructs can be constructed in a similar manner as those described above that comprise other metabolic interference genes located in the vector backbone. Examples of these include, but are not limited to polynucleotides that encode for yeast invertase (SEQ ID NO:6) and yeast trehalose-6-phosphate synthase (SEQ ID NO:7).

Example 2

Crop Transformation

The DNA constructs described in the present invention (e.g., pMON42066, pMON75181, pMON75182 and pMON75183) are transformed into a disarmed *Agrobacterium* strain. The DNA construct is transferred into *Agrobacterium*, for example, by a triparental mating method (Ditta et al., Proc. Natl. Acad. Sci. 77:7347-7351, 1980), or by electroporation. Liquid cultures of *Agrobacterium* are initiated from glycerol stocks or from a freshly streaked plate and grown overnight at 26° C.-28° C. with shaking (approximately 150 rpm) to mid-log growth phase in liquid LB medium, pH 7.0 containing the appropriate antibiotics. The *Agrobacterium* cells are resuspended in the inoculation medium and the density is adjusted to $OD_{660}$ of about 1.

Transformation of corn cells and regeneration of the cells into intact fertile plants by *Agrobacterium* mediated transformation can be conducted using various methods known in the art. For example, surface sterilized corn seeds are germinated and cut seedlings into pieces. Place each seedling piece with the wounded surface down on semi-solid callus induction MSW57 medium, 10 to 16 pieces per Petri plate, incubate plates in a lighted Percival incubator (16 hour photoperiod), 28° C. After 2 to 4 weeks, transfer the embryogenic calli to fresh MSW57 medium, incubate in the dark at 28° C. for 2-3 weeks.

Select callus pieces that have been sub-cultured 6-8 days previously, in a Petri plate (100 mm×25 mm). Each plate may contain 300-500 pieces of calli. Add 1 μl of F-68 (Pluronic F-68 solution 10%, Sigma-Aldrich, St Louis, Mo.) per 1 ml of *Agrobacterium* cell suspension (the *Agrobacterium* containing a DNA plasmid of the present invention), then add enough of this suspension to cover the tissue. Incubate for 5-20 minutes at room temperature. Remove *Agrobacterium* suspension with a fine-tipped transfer pipette. Dump the callus pieces in a Petri plate, with 3 pieces of sterile filter paper (Whatman #1, 8.5 or 9 cm in diameter) on the bottom and 2 pieces of filter paper on the top. Blot them briefly upside down a few times. Transfer the callus pieces (60-100 each) into one Petri plate with 1 piece of filter paper without water or medium and seal the dish with parafilm. Incubate the plate in the dark at 23° C. for 2-3 days.

Prepare culture plates by placing 2 pieces of felt (2 cm×2 cm squares) in each Petri plate with 23-25 ml of the MSW57/C500/P100 (carbenicillin 500 mg/L, paromomycin 100 mg/L) medium, see Table 1 for media components. Transfer the callus pieces into the culture plates. During transfer, separate the callus into small pieces (2-3 mm), each culture plate may contain 16-25 callus pieces. Incubate the culture plates in the dark at 27° C. for approximately 2 weeks. Remove the selection medium, then add 18-20 ml of fresh medium. Incubate the plates in the dark at 27° C. for approximately 2 weeks. Remove the selection medium and replace with 18-20 ml of MS/6BA/C250/P100 medium (tissue transformed with DNA plasmids that included the codA gene was transferred to media that contained from 25 mg/L to 1000 mg/l 5-fluorocytosine). Move the plates to a lighted incubator (16-h light, 27° C.) for 5-7 days, then move the growing tissues to MSOD/C250/P100 solid medium. Incubate approximately 2 wks on this medium. Callus pieces will have regenerated green shoots with or without roots. Those shoots should be healthy looking and easily distinguishable from some small shoots. Transfer the healthy shoots onto MSOD/C250/P100 solidified with 3 g/l Phytagar. During transfer, remove callus tissue attached to the root area of the shoots, incubate to enlarge shoots and roots, then transfer to soil.

TABLE 1

| Media components | |
|---|---|
| amount/L | |
| MSW57 | |
| Pre-autoclaving ingredients | |
| 4.4 g | Gibco MS (500-1117EH) |
| 10 ml | MS Vitamins 100X (Sigma M-7150) |
| 1.25 ml | Thiamine HCl (0.4 mg/ml) |
| 30 g | Sucrose (Sigma S-5391) |
| 1.38 g | 1-Proline (Sigma P-4655) |
| 0.5 g | Casamino Acids (DifCo DF0288-01-2) |
| 3.0 g | Phytagel (Sigma P-8169) |
| Post-autoclaving ingredients | |
| 0.5 ml | 2,4-D (1 mg/ml) |
| 2.2 ml | Pichloram (1 mg/ml) |
| 1.7 ml | Silver Nitrate (2 mg/ml) |
| MS0D/C250/P100 | |
| Pre-autoclaving ingredients | |
| 4.4 g | Gibco MS (500-1117EH) |
| 1 ml | MS Fromm 1000X |
| 10 g | Glucose (PhytaTech G386) |
| 20 g | Maltose (PhytaTech M588) |
| 0.15 g | 1-Asparagine (Sigma A-4284) |
| 0.01 g | Myo-inositol (Sigma I-3011) |
| 6.0 g | Phytagar (10675-031) |
| Post-autoclaving ingredients | |
| 2 ml | Paromomycin (50 mg/ml) |
| 1 ml | Carbenicillin (250 mg/ml) |
| MS/6BA/P100/C250 | |
| Pre-autoclaving ingredients | |
| 4.4 g | Gibco MS (500-1117EH) |
| 10 ml | MS Vitamins 100X (Sigma M-7150) |
| 1.25 ml | Thiamine HCl (0.4 mg/ml) |
| 7.04 ml | BAP (0.5 mg/ml) |
| 30 g | Sucrose (Sigma S-5391) |
| 1.38 g | 1-Proline (Sigma P-4655) |
| 0.5 g | Casamino Acids (DifCo DF0288-01-2) |

TABLE 1-continued

| Media components | |
|---|---|
| amount/L | |
| Post-autoclaving ingredients | |
| 2 ml | Paromomycin (50 mg/ml) |
| 1 ml | Carbenicillin (250 mg/ml) |

Dicot plant cells can be transformed and regenerated into intact plants by methods known in the art of plant transformation and tissue culture. The use of *Agrobacterium*-mediated methods to transfer the T-DNA of the plasmids of the present invention are well known in the art. For example cotton (U.S. Pat. No. 5,004,863; U.S. Pat. No. 5,159,135; U.S. Pat. No. 5,518,908, herein incorporated by reference), soybean (U.S. Pat. No. 5,569,834; U.S. Pat. No. 5,416,011, herein incorporated by reference).

The above transformation and regeneration methods provides for plants that are greatly reduced in the occurrence of vector backbone DNA. Additionally, the plants have an added benefit of having reduced copy number of the insert T-DNA. The plants produced by the method are an aspect of the invention.

Example 3

Molecular Analysis for Backbone DNA and Copy Number

DNA is extracted from tissue samples removed from plants transformed with the DNA plasmids of the present invention and regenerated from plant cell tissue culture. A PCR based method is used to assay the DNA for the presence of the Ec.oriV DNA segment, an indicator of vector backbone. This DNA is adjacent to the LB and its presence in the DNA extracted from the regenerated plants indicates that transfer of vector sequences beyond the LB has occurred. DNA can be isolated from plant tissues by any number of methods for example, the CTAB procedure (Rogers et at., Plant Mol. Biol. 5:69-76, 1985) or DNAeasy™ 96 Plant Kit (Cat. #69181, Qiagen Inc., Valencia, Calif.) following the manufacturers instructions. Taqman® (PE Applied Biosystems, Foster City, Calif.) is described as a method of detecting and quantifying the presence of a DNA sequence and is fully understood in the instructions provided by the manufacturer. DNA primer molecules listed in Table 2 are used in the described method to identify the Ec.oriV DNA from plant extracts. The conditions and apparatus used can be modified by those skilled in the art to provide the same results.

Figure 14:
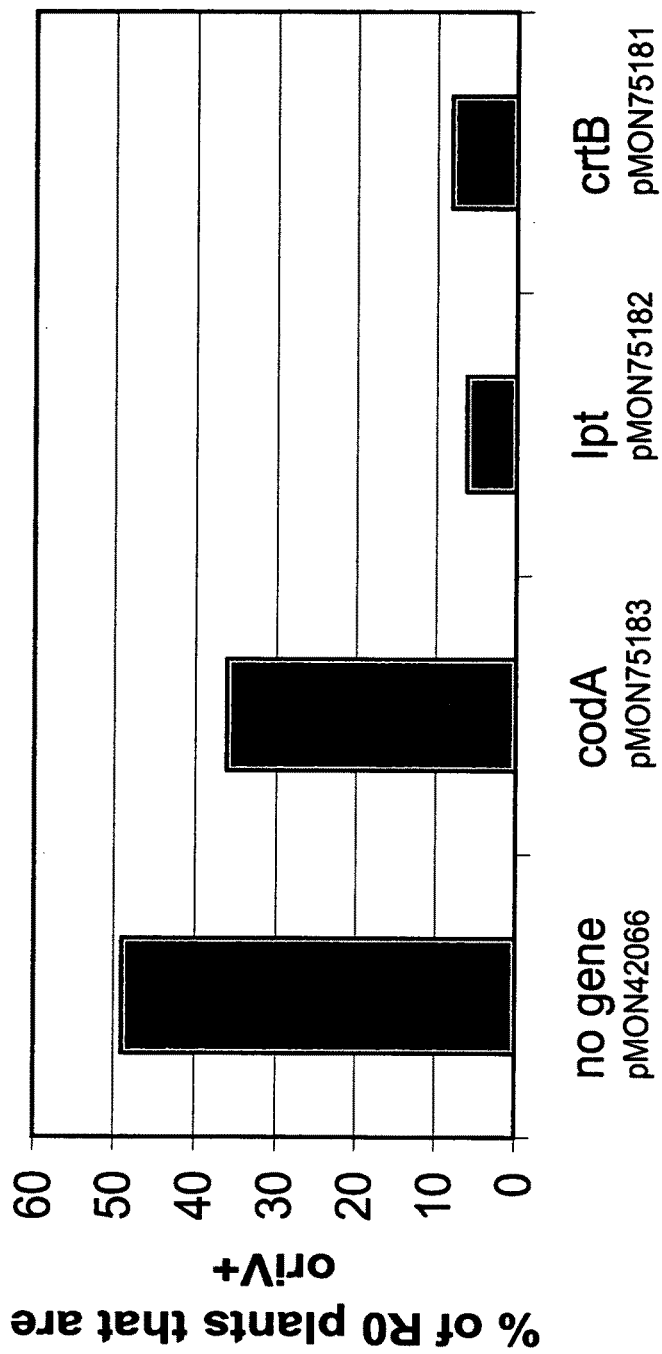

Corn plant cells were transformed with a control DNA plasmid (pMON42066), a DNA plasmid with a conditional lethal gene in the vector backbone (pMON75183), a DNA plasmid with a non-lethal selectable marker gene (ipt, pMON75182), and a DNA plasmid with a non-lethal selectable marker gene (crtB, pMON75181), then regenerated into intact plants. The intact plants were analyzed for the presence of Ec.oriV. FIG. 14 shows the results of this analysis. Approximately half of the thirty-five plants that are regenerated after transformation with the control plasmid (no gene, pMON42066) are positive for the Ec.oriV DNA, and approximately thirty-five percent of the seventy-seven plants transformed with the conditional lethal gene plasmid (codA, pMON75183). Surprisingly, the non-lethal negative selectable marker genes, ipt and crtB, provide expectional reduction in the occurrence of transgenic plants with Ec.oriV DNA. Only five percent of the eight-three plants transformed with pMON75182 contained the Ec.oriV DNA, and only eight percent of the sixty-one plants transformed with pMON75181.

These results demonstrate the substantial benefit conferred by the DNA plasmids of the present invention by reducing the occurrence of vector backbone. Nearly half of the plants transformed with the conventional DNA plasmid configuration (pMON42066) will be discarded. Of the plants transformed with the DNA plasmids (pMON75182, pMON75181) of the present invention, less than ten percent would be discarded.

TABLE 2

| Ec.OriV Endpoint Taqman ® Assay-10uL Reaction | | | | | |
|---|---|---|---|---|---|
| Element | primer/probe Final conc | Working stock conc | volume | Multiplier | Mastermix Volume |
| Universal master mix | | | 5 | 70 | 350 |
| H20 | | | 1.8 | 70 | 126 |
| OriV-F SEQ ID NO: 8 | 0.4 uM | 20 uM | 0.2 | 70 | 14 |
| OriV-R SEQ ID NO: 9 | 0.4 uM | 20 uM | 0.2 | 70 | 14 |
| LGI-F SEQ ID NO: 11 | 0.4 uM | 20 uM | 0.2 | 70 | 14 |
| LGI-R SEQ ID NO: 12 | 0.4 uM | 20 uM | 0.2 | 70 | 14 |
| OriV-FAM MGB probe SEQ ID NO: 10 | 0.1 uM | 5 uM | 0.2 | 70 | 14 |
| LGI VIC probe SEQ ID NO: 13 | 0.1 uM | 5 uM | 0.2 | 70 | 14 |
| DNA sample | | | 2 | | |
| | | | 10 uL Reaction | | |
| Conditions: MJ Engine | | | | | |
| | 50 C. | 2:00 | 1 cycle | | |
| | 95 C. | 10:00 | 1 cycle | | |
| | 95 C. | 0:15 | 1 cycle | | |
| | 56 C. | 1:00 | 35 cycles | | |

Figure 15:
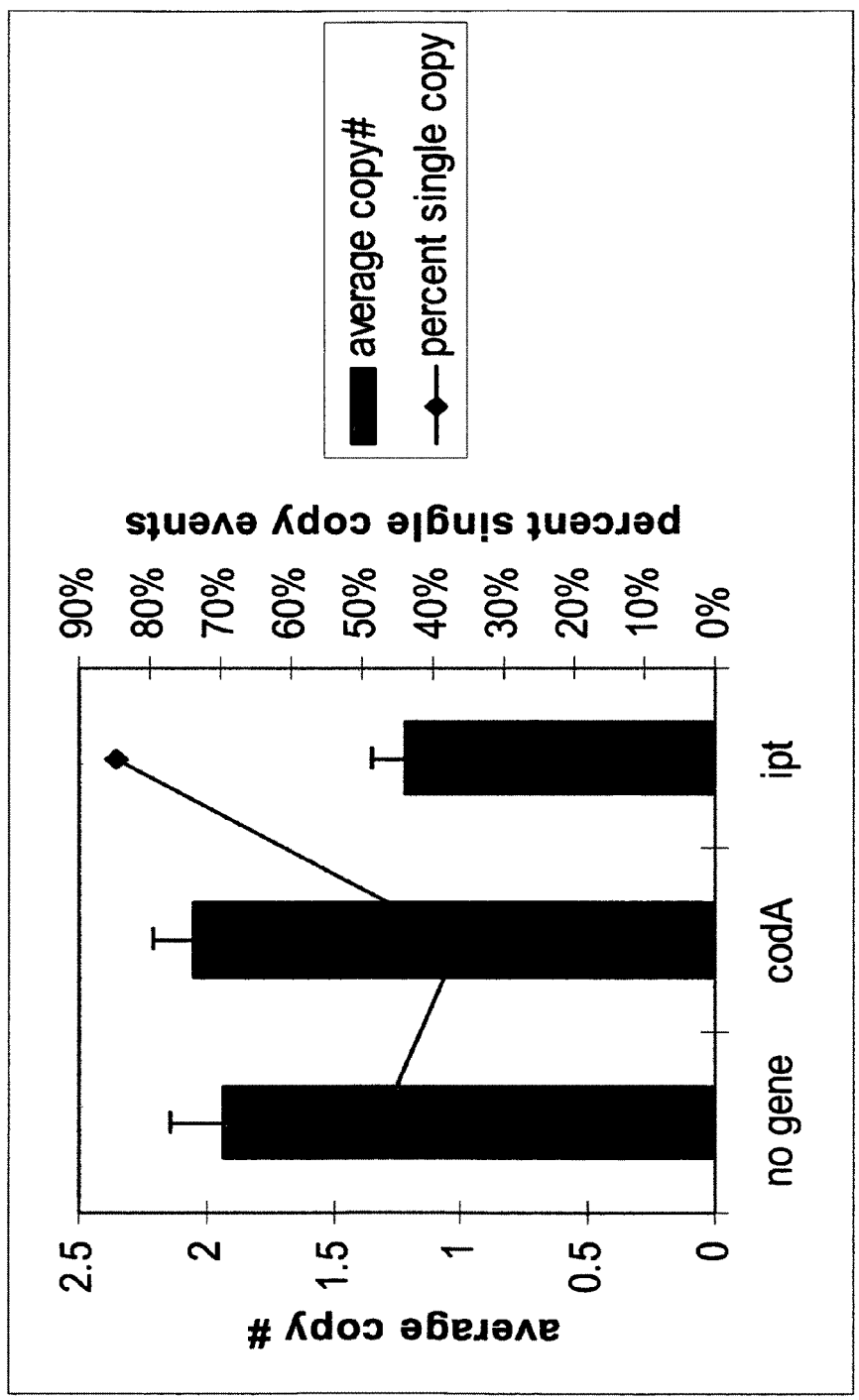
FIG. 15. Effect of non-lethal selectable marker gene (crtB) on the insert copy number of corn plants transformed with pMON75181 (crtB) and pMON75182 (ipt).

Another important component of a commercially viable transgenic plant is the occurrence of low insert complexity. This is often referred to as a low copy number. It is difficult to select progeny and to successfully breed the transgenic trait if the copy number of the insert is too high. Ideally, only a single copy of the transgene would be present in a transgenic event. Copy number can be determined by several methods known in the art of molecular biology. Southern blot analysis is the most commonly used method. Methods using the Taqman® technology are also accurate and reliable for determining copy number of T-DNA inserts in transgenic plants. The method and DNA primer molecules outlined in Table 3 shows how to assay plants for the presence of the nptII coding sequence. The expression cassette containing the nptII selectable marker gene is present in pMON42066, pMON75183, and pMON75182. Plants transformed with these DNA plasmids are assayed by a Taqman® method for copy number and the results are shown in FIG. 15. The no gene in backbone (pMON42066) plasmid shows that the average copy number of the thirty-four plants assayed is about two and only forty-seven percent are single copy. The conditional lethal selectable marker (codA, pMON75183) plasmid shows that the average copy number of the fifty plants assayed is about two and only thirty-six percent of the plants were single copy. The non-lethal selectable marker gene (ipt, pMON75182) plasmid shows that the average copy number of the twenty-seven plants assayed is 1.2 and surprisingly, eight-five percent of the transgenic plants are single copy. This result shows the value of the plasmids of the present invention for reducing transgene copy number.

TABLE 3

NPT II Taqman ® Assay for ABI 7900 (384 well format)

| Element | primer/probe Final conc | primer stock conc | volume | Multiplier | Mastermix Volume |
|---|---|---|---|---|---|
| Universal master mix | | | 5 | 500 | 2500 |
| H20 | | | 1.3 | 500 | 650 |
| NPT II FP SEQ ID NO: 14 | 0.3 uM | 10 uM | 0.3 | 500 | 150 |
| NPT II RP SEQ ID NO: 15 | 0.3 uM | 10 uM | 0.3 | 500 | 150 |
| LGI F SEQ ID NO: 11 | 0.15 uM | 10 uM | 0.15 | 500 | 75 |
| LGI R SEQ ID NO: 12 | 0.15 uM | 10 uM | 0.15 | 500 | 75 |
| NPT II-FAM SEQ ID NO: 16 | 200 nM | 5 uM | 0.4 | 500 | 200 |
| LGI-VIC SEQ ID NO: 13 | 200 nM | 5 uM | 0.4 | 500 | 200 |
| DNA sample | | | 2 | | |
| | | | 10 uL Reaction | | |

Conditions: MJ engine

| Temp | Time | Cycle |
|---|---|---|
| 50 C. | 2:00 | 1 cycle |
| 95 C. | 10:00 | 1 cycle |
| 95 C. | 0:15 | |
| 56 C. | 1:00 | 40 cycles |

Figure 18:
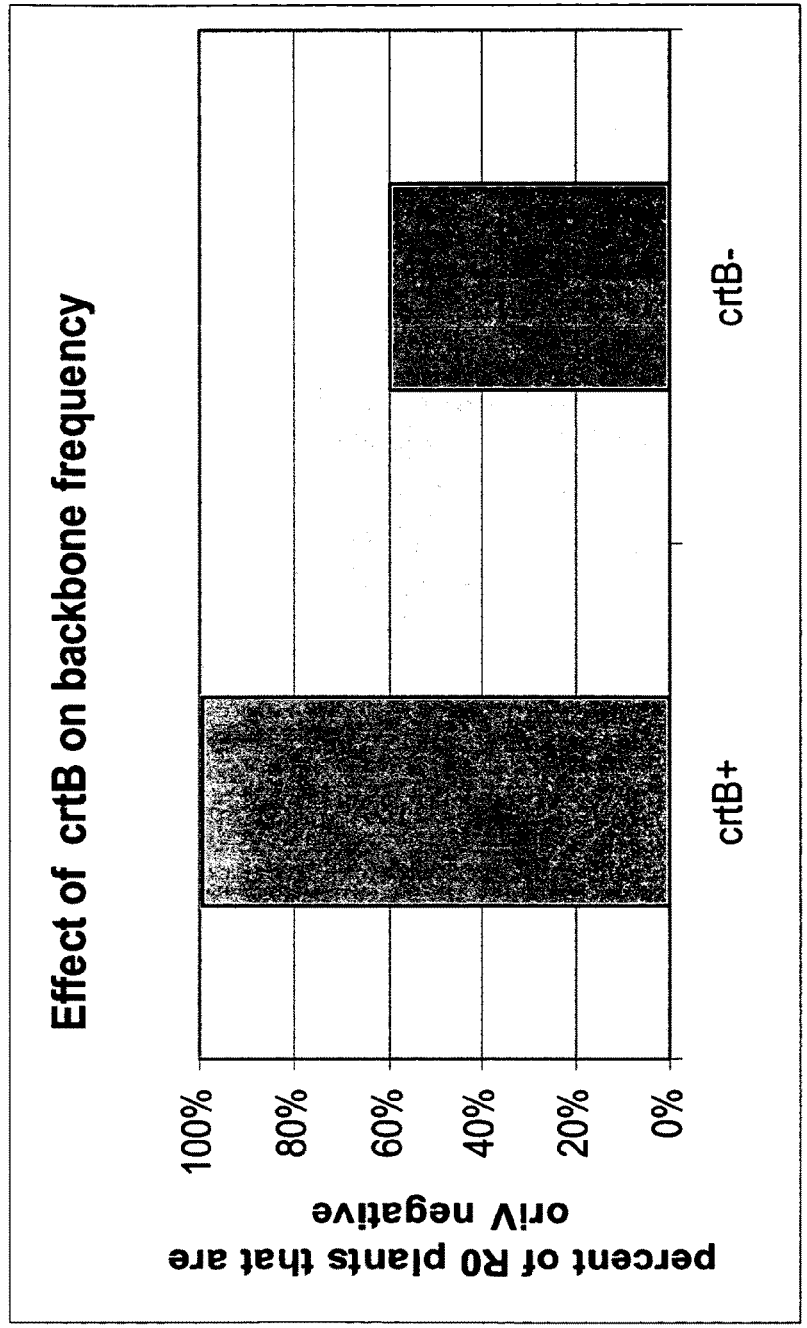
Figure 19:
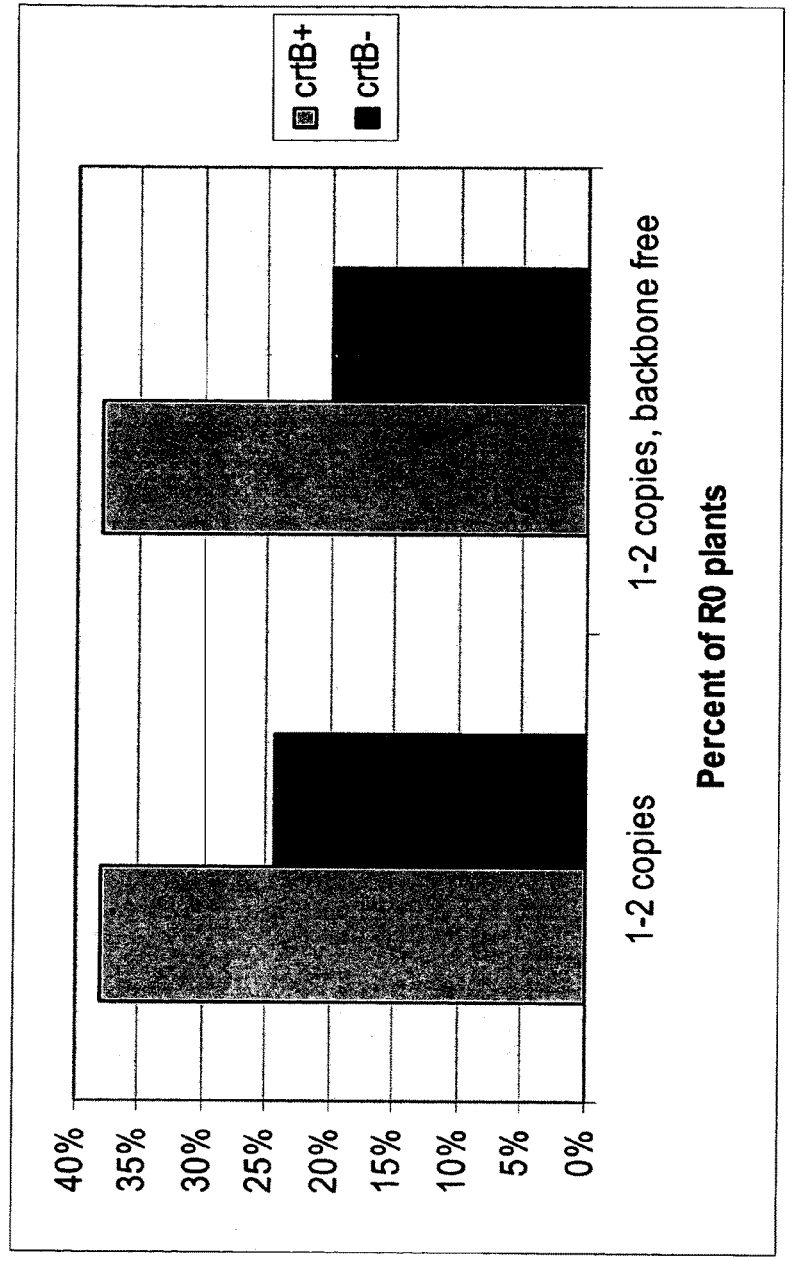
FIG. 19. Effect of non-lethal selectable marker gene on the insert copy number of corn plants transformed with pMON73565 (crtB+).

The DNA constructs, pMON73564 and pMON73565, were transformed into corn cells, for example, using the method previously described. The resulting transgenic corn plants were assayed for presence of the backbone DNA using the conditions previously described for detection of Ec.oriV DNA. The results illustrated in FIG. 18 show that nearly all of the plants (N=104) regenerated after transformation with pMON73565 (crtB+, non-lethal selectable marker gene in the backbone) were free of the Ec.oriV. Forty percent of the plants (N=115) transformed with the control construct, pMON73564 (crtB−, no marker gene in the backbone), had the Ec.oriV DNA in their genome. The same set of plants was assayed for copy number, the results illustrated in FIG. 19. These results show that substantially more plants transformed with pMON73565 (crtb+ construct) had low copy number and were backbone free compared to the plants transformed with the pMON73564 construct that did not contain the non-lethal selectable marker gene in the backbone. These results demonstrate the utility of a non-lethal selectable marker gene in the DNA construct for providing substantially more plants of commercial quality.

Figure 22:
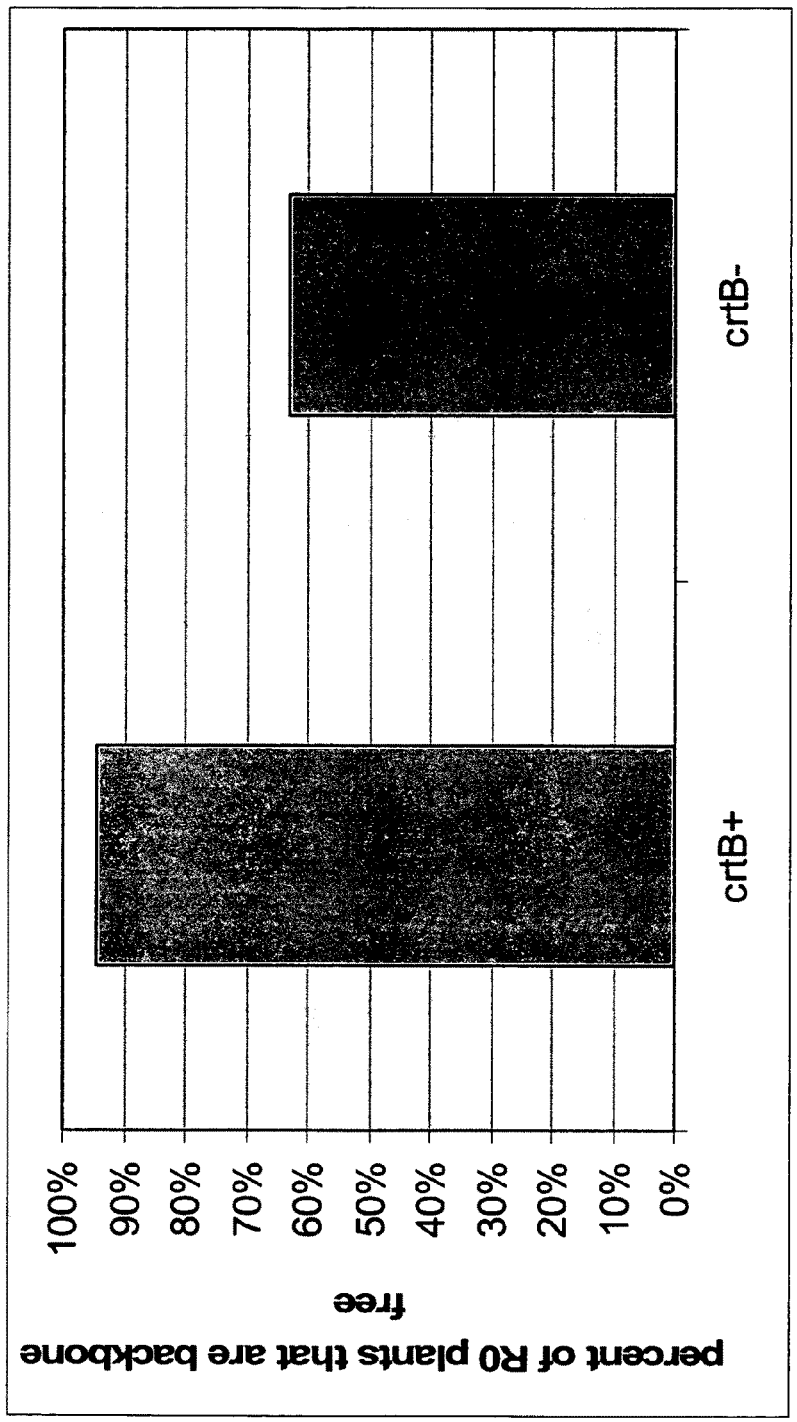
Figure 23:
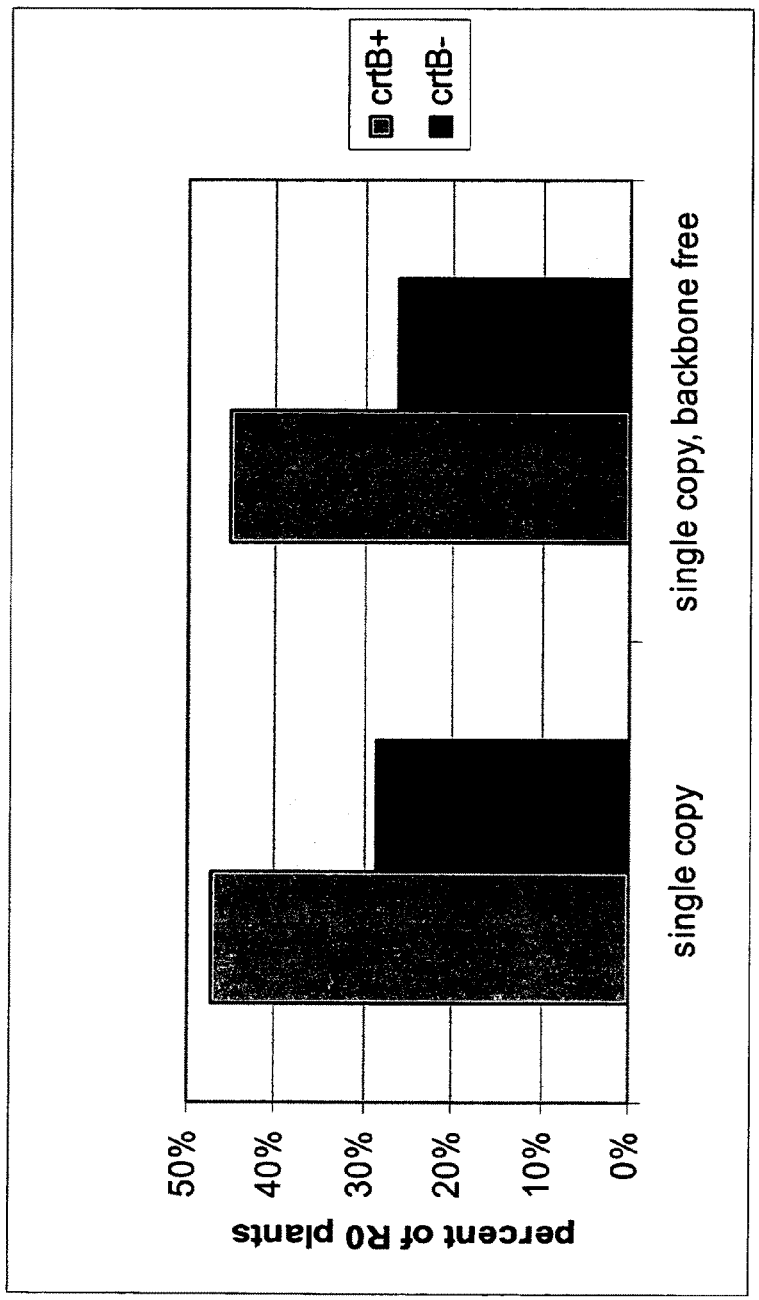
FIG. 23. Effect of non-lethal selectable marker gene on the insert copy number of corn plants transformed with pMON67936 (crtB+).

Additional evidence is provided of the utility of the non-lethal selectable marker gene contained in the vector backbone from data collected from corn cells transformed with the DNA constructs, pMON67935 and pMON67936, for example, by the transformation method previously described. The resulting transgenic corn plants were assayed for the presence of the backbone DNA using conditions previously described for detection of Ec.oriV DNA. The results illustrated in FIG. 22 show that greater than 90 percent of the plants (N+54) regenerated after transformation with pMON67936 (crtB+, non-lethal selectable marker gene in the backbone) were free of Ec.oriV. About 40 percent of the plants (N=84) transformed with the control construct, pMON67935 (crtB−, no marker gene in the backbone) had the Ec.oriV DNA in their genome. The same set of plants was assayed for copy number, the results illustrated in FIG. 23. These results show that substantially more plants transformed with pMON67936 (crtB+ construct) had low copy number and were backbone free compared to the plants transformed with the pMON67935 construct that did not contain the non-lethal selectable marker gene in the backbone. These results demonstrate the utility of a non-lethal selectable marker gene in the DNA construct for providing substantially more plants of commercial quality.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

We claim:

1. A DNA plasmid comprising a T-DNA comprising an *Agrobacterium* Ti plasmid first border region linked to at least one transgene linked to an *Agrobacterium* Ti plasmid second border region, and located in the DNA plasmid outside of the T-DNA is a plant expression cassette comprising a plant cell non-lethal negative selectable marker gene linked to a vector backbone DNA, wherein the plant cell non-lethal negative selectable marker gene is a cytokinin oxidase gene.

2. The DNA plasmid of claim 1, wherein said plant expression cassette comprises a promoter that functions in plant cells operably linked to the plant cell non-lethal negative selectable maker gene.

3. The DNA plasmid of claim 2, wherein said promoter is a constitutive promoter.

4. The DNA plasmid of claim 2, wherein said promoter induces expression of said linked non-lethal negative selectable maker gene product in tissue culture during plant regeneration.

5. The DNA plasmid of claim 1, wherein said transgene is a plant positive selectable marker gene selected from the group consisting of antibiotic resistance and herbicide resistance.

6. The DNA plasmid of claim 1, wherein said transgene comprises a transgene of agronomic interest.

7. A method for enhancing the selection of transgenic plants that do not contain vector backbone DNA comprising the steps of: a) transforming a plurality of plant cells with the DNA plasmid of claim 5; and b) selecting said plant cells on a positive selection compound; and c) regenerating said selected plant cells into plants.

8. A method for reducing the copy number of a transgene in a plant cell comprising the steps of: a) transforming a plurality of plant cells with the DNA plasmid of claim 5; and b) selecting said transformed plant cells on a positive selection compound; and c) regenerating said selected plant cells into plants.

* * * * *